(12) United States Patent
Harr et al.

(10) Patent No.: US 8,052,642 B2
(45) Date of Patent: Nov. 8, 2011

(54) PUMPING APPARATUS WITH SECURE LOADING FEATURES

(75) Inventors: James M. Harr, Foristell, MO (US);
Joel D. Wiesner, St. Peters, MO (US);
Christopher A. Knauper, Lake Saint Louis, MO (US); Glenn G. Fournie, Smithton, IL (US); Ricky A. Sisk, Washington, MO (US); Joseph A. Hudson, O'Fallon, MO (US); Robert B. Gaines, Lake Saint Louis, MO (US); Kevin C. Meier, St. Louis, MO (US); James G. Hanlon, Morgan Hill, CA (US)

(73) Assignee: Covidien AG (CH)

( * ) Notice: Subject to any disclaimer, the term of this patent is extended or adjusted under 35 U.S.C. 154(b) by 0 days.

(21) Appl. No.: 12/616,205

(22) Filed: Nov. 11, 2009

(65) Prior Publication Data

US 2010/0056994 A1 Mar. 4, 2010

Related U.S. Application Data

(63) Continuation of application No. 11/366,226, filed on Mar. 2, 2006, now Pat. No. 7,722,573.

(51) Int. Cl.
*A61M 31/00* (2006.01)
*A61M 1/00* (2006.01)
*A61M 37/00* (2006.01)
*A61B 5/00* (2006.01)

(52) U.S. Cl. ........ 604/131; 604/151; 604/153; 604/154; 604/67; 600/310

(58) Field of Classification Search ............... 604/249, 604/250, 151
See application file for complete search history.

(56) References Cited

U.S. PATENT DOCUMENTS 2,483,924 A 10/1949 Moulinier
3,432,128 A 3/1969 Elleboudt
(Continued)

FOREIGN PATENT DOCUMENTS

DE 3627011 A1 2/1988
(Continued)

OTHER PUBLICATIONS

European Search Report for EP 0815374.4 dated Sep. 11, 2008, 3 pgs.
(Continued)

*Primary Examiner* — Nicholas D Lucchesi
*Assistant Examiner* — Ian K Holloway
(74) *Attorney, Agent, or Firm* — Elias Domingo

(57) ABSTRACT

A pumping apparatus and pump set for use to deliver a supply of liquid to a patient. The feeding set has a conduit for the nutrient liquid and a safety interlock device associated with the conduit. The pumping apparatus has a pumping device and a control system for controlling operation of the pump. An electromagnetic radiation source is operatively connected to the control system of the pump for emitting an electromagnetic radiation signal in a direction for striking the safety interlock device of the feeding set. The safety interlock device being adapted to affect the direction of the electromagnetic radiation. An electromagnetic radiation detector is operatively connected to the control system for receiving the electromagnetic radiation signal when the direction is affected by the safety interlock device, and provides an indication to the control system that the feeding set conduit is properly positioned in the feeding pump.

7 Claims, 24 Drawing Sheets

U.S. PATENT DOCUMENTS

| | | |
|---|---|---|
| 3,435,209 A | 3/1969 | Keahl |
| 3,523,179 A | 8/1970 | Edwards et al. |
| 3,673,476 A | 6/1972 | Hamburg |
| 3,675,653 A | 7/1972 | Crowley et al. |
| 3,693,025 A | 9/1972 | Brunton |
| 3,851,976 A | 12/1974 | Meier |
| 3,982,162 A | 9/1976 | Olliffe |
| 3,985,133 A | 10/1976 | Jenkins et al. |
| 3,987,303 A | 10/1976 | Stoft et al. |
| 3,993,061 A | 11/1976 | O'Leary |
| 4,038,982 A | 8/1977 | Burke et al. |
| 4,126,132 A | 11/1978 | Portner et al. |
| 4,300,048 A | 11/1981 | Barbier et al. |
| 4,346,296 A | 8/1982 | Passaro et al. |
| 4,424,011 A | 1/1984 | O'Brien et al. |
| 4,454,763 A | 6/1984 | Mahler |
| 4,504,263 A | 3/1985 | Steuer et al. |
| 4,508,422 A | 4/1985 | Karlsson |
| 4,525,069 A | 6/1985 | Tanaka et al. |
| 4,537,561 A | 8/1985 | Xanthopoulos |
| 4,646,144 A | 2/1987 | Ishida et al. |
| 4,652,260 A | 3/1987 | Fenton, Jr. et al. |
| 4,665,391 A | 5/1987 | Spani |
| 4,714,463 A | 12/1987 | Archibald et al. |
| 4,720,636 A | 1/1988 | Benner, Jr. |
| 4,763,032 A | 8/1988 | Bramm et al. |
| 4,785,322 A | 11/1988 | Harrison et al. |
| 4,788,444 A | 11/1988 | Williams |
| 4,792,424 A | 12/1988 | Loman |
| 4,797,655 A | 1/1989 | Orndal et al. |
| 4,806,751 A | 2/1989 | Abe et al. |
| 4,845,487 A | 7/1989 | Frantz et al. |
| 4,845,489 A | 7/1989 | Hormel |
| 4,850,807 A | 7/1989 | Frantz |
| 4,878,896 A | 11/1989 | Garrison et al. |
| 4,882,575 A | 11/1989 | Kawahara |
| 4,884,013 A | 11/1989 | Jackson et al. |
| 4,884,065 A | 11/1989 | Crouse et al. |
| 4,909,797 A | 3/1990 | Timothy |
| 4,913,703 A | 4/1990 | Pasqualucci et al. |
| 4,933,563 A | 6/1990 | Thus |
| 4,940,050 A | 7/1990 | Forssmann et al. |
| 4,944,748 A | 7/1990 | Bramm et al. |
| 4,945,244 A | 7/1990 | Castleman |
| 4,950,235 A | 8/1990 | Slate et al. |
| 4,958,910 A | 9/1990 | Taylor et al. |
| 4,976,590 A | 12/1990 | Baldwin |
| 5,055,001 A | 10/1991 | Natwick et al. |
| 5,057,081 A | 10/1991 | Sunderland et al. |
| 5,058,970 A | 10/1991 | Schildkraut et al. |
| 5,101,711 A | 4/1992 | Durbin |
| 5,181,842 A | 1/1993 | Sunderland et al. |
| 5,207,645 A | 5/1993 | Ross et al. |
| 5,211,626 A | 5/1993 | Frank et al. |
| 5,237,450 A | 8/1993 | Stromberg |
| 5,250,027 A | 10/1993 | Lewis et al. |
| 5,256,155 A | 10/1993 | Yerlikaya et al. |
| 5,330,431 A | 7/1994 | Herskowitz |
| 5,336,174 A | 8/1994 | Daoud et al. |
| 5,352,364 A | 10/1994 | Kruger et al. |
| 5,357,113 A | 10/1994 | Liston et al. |
| 5,364,364 A | 11/1994 | Kasvikis et al. |
| 5,383,858 A | 1/1995 | Reilly et al. |
| 5,415,641 A | 5/1995 | Yerlikaya et al. |
| 5,433,588 A | 7/1995 | Monk et al. |
| 5,436,455 A | 7/1995 | Rosenthal et al. |
| 5,437,635 A | 8/1995 | Fields et al. |
| 5,502,111 A | 3/1996 | Huynh-Ba |
| 5,508,521 A | 4/1996 | Kraft et al. |
| 5,531,680 A | 7/1996 | Dumas et al. |
| 5,531,697 A | 7/1996 | Olsen et al. |
| 5,533,453 A | 7/1996 | Wolfberg et al. |
| 5,536,935 A | 7/1996 | Klotzsch et al. |
| 5,560,355 A | 10/1996 | Merchant et al. |
| 5,567,120 A * | 10/1996 | Hungerford et al. ............ 417/63 |
| 5,569,026 A | 10/1996 | Novak |
| 5,575,284 A | 11/1996 | Athan et al. |
| 5,584,671 A | 12/1996 | Schweitzer, Jr. et al. |
| 5,586,567 A | 12/1996 | Smith et al. |
| 5,602,664 A | 2/1997 | Doyle |
| 5,604,020 A | 2/1997 | Fitchmun |
| 5,620,312 A | 4/1997 | Hyman et al. |
| 5,623,907 A | 4/1997 | Cotton et al. |
| 5,626,129 A | 5/1997 | Klimm et al. |
| 5,631,730 A | 5/1997 | Chupp et al. |
| 5,634,907 A | 6/1997 | Rani et al. |
| 5,661,231 A | 8/1997 | Koskela |
| 5,681,284 A | 10/1997 | Herskowitz |
| 5,683,367 A | 11/1997 | Jordan et al. |
| 5,704,912 A | 1/1998 | Lawrence et al. |
| 5,711,654 A | 1/1998 | Afflerbaugh |
| 5,721,430 A | 2/1998 | Wong |
| 5,752,813 A | 5/1998 | Tyner et al. |
| 5,767,976 A | 6/1998 | Ankerhold et al. |
| 5,788,674 A | 8/1998 | McWilliams |
| 5,795,327 A | 8/1998 | Wilson et al. |
| 5,798,699 A | 8/1998 | Bryant et al. |
| 5,818,049 A | 10/1998 | Bailey et al. |
| 5,828,458 A | 10/1998 | Taylor et al. |
| 5,851,631 A | 12/1998 | Borden et al. |
| 5,853,386 A | 12/1998 | Davis et al. |
| 5,882,338 A | 3/1999 | Gray |
| 5,903,006 A | 5/1999 | Kiuchi et al. |
| 5,920,018 A | 7/1999 | Wilkerson et al. |
| 6,013,020 A | 1/2000 | Meloul et al. |
| 6,015,272 A | 1/2000 | Antaki et al. |
| 6,023,970 A | 2/2000 | Blaine |
| 6,067,463 A | 5/2000 | Jeng et al. |
| 6,078,042 A | 6/2000 | Fellows |
| 6,095,986 A | 8/2000 | Braig et al. |
| 6,099,502 A | 8/2000 | Duchon et al. |
| 6,106,498 A | 8/2000 | Friedli et al. |
| 6,117,115 A | 9/2000 | Hill et al. |
| 6,129,699 A | 10/2000 | Haight et al. |
| 6,162,183 A | 12/2000 | Hoover |
| 6,219,138 B1 | 4/2001 | Swanson et al. |
| 6,227,817 B1 | 5/2001 | Paden |
| 6,244,835 B1 | 6/2001 | Antaki et al. |
| 6,263,227 B1 | 7/2001 | Boggett et al. |
| 6,299,600 B1 | 10/2001 | Masaoka et al. |
| 6,325,422 B1 | 12/2001 | Verkaart et al. |
| 6,390,590 B1 | 5/2002 | Hansburg |
| 6,437,316 B1 | 8/2002 | Colman et al. |
| 6,461,323 B2 | 10/2002 | Fowler et al. |
| 6,494,692 B1 | 12/2002 | Green |
| 6,523,414 B1 | 2/2003 | Malmstrom et al. |
| 6,528,791 B1 | 3/2003 | Williams et al. |
| 6,531,708 B1 | 3/2003 | Malmstrom et al. |
| 6,552,145 B1 | 4/2003 | Okada et al. |
| 6,585,684 B1 | 7/2003 | Hughett et al. |
| 6,617,175 B1 | 9/2003 | Arno |
| 6,626,862 B1 | 9/2003 | Duchon et al. |
| 6,635,033 B1 * | 10/2003 | Hill et al. ...................... 604/249 |
| 6,659,976 B2 | 12/2003 | Beck et al. |
| 6,661,482 B2 | 12/2003 | Hara |
| 6,683,679 B2 | 1/2004 | Belenkii |
| 6,747,276 B2 | 6/2004 | Watanabe |
| 6,786,879 B1 | 9/2004 | Bolam et al. |
| 6,811,382 B2 | 11/2004 | Buchanan et al. |
| 6,890,291 B2 | 5/2005 | Robinson et al. |
| 6,891,343 B2 | 5/2005 | Petersen |
| 6,900,449 B2 | 5/2005 | Bolash et al. |
| 6,949,066 B2 | 9/2005 | Bearnson et al. |
| 6,958,053 B1 | 10/2005 | Reilly |
| 7,009,150 B2 | 3/2006 | Wennemann et al. |
| 7,018,363 B2 | 3/2006 | Cowan et al. |
| 7,041,082 B2 | 5/2006 | Blomquist et al. |
| 7,092,796 B2 | 8/2006 | Vanderveen |
| 7,126,495 B2 | 10/2006 | Netzer |
| 7,144,384 B2 | 12/2006 | Gorman et al. |
| 7,145,127 B2 | 12/2006 | Chin et al. |
| 7,258,534 B2 | 8/2007 | Fathallah et al. |
| 7,462,170 B2 | 12/2008 | Fournie et al. |
| 7,537,579 B2 | 5/2009 | Price |
| 7,570,428 B2 | 8/2009 | Watanabe |
| 7,578,782 B2 | 8/2009 | Miles et al. |
| 7,591,980 B2 | 9/2009 | Call et al. |

| | | | |
|---|---|---|---|
| 7,632,248 B2 | 12/2009 | Delk et al. | |
| 7,763,005 B2 | 7/2010 | Knauper et al. | |
| 2002/0036276 A1 | 3/2002 | Seeman | |
| 2004/0036273 A1 | 2/2004 | McClary | |
| 2004/0158205 A1 | 8/2004 | Savage | |
| 2005/0186377 A1 | 8/2005 | Hurst et al. | |
| 2005/0267439 A1 | 12/2005 | Harr et al. | |
| 2007/0208304 A1 | 9/2007 | Hudson et al. | |
| 2007/0208305 A1 | 9/2007 | Wiesner et al. | |
| 2007/0253833 A1 | 11/2007 | Hanlon et al. | |
| 2009/0284603 A1 | 11/2009 | Hsieh | |

FOREIGN PATENT DOCUMENTS

| | | |
|---|---|---|
| DE | 3910250 A1 | 10/1990 |
| EP | 0467805 B1 | 3/1995 |
| EP | 0563351 B1 | 12/1997 |
| EP | 0718006 B1 | 3/1999 |
| EP | 0891784 B1 | 9/2003 |
| EP | 0876825 B1 | 2/2005 |
| ES | 8500067 A1 | 1/1985 |
| GB | 2065916 A | 7/1981 |
| JP | 2006233014 A | 9/2006 |
| WO | 9320440 A1 | 10/1993 |
| WO | 9320441 A1 | 10/1993 |
| WO | 9508774 A2 | 3/1995 |
| WO | 9844320 A1 | 10/1998 |
| WO | 2004028595 A1 | 4/2004 |

OTHER PUBLICATIONS

Garcia, et al: "Computational Prediction of PVC Degradation During Injection Molding in a Rectangular Channel", Polymer Engineering & Science, Jul. 2004, vol. 44, No. 7, pp. 1295-1312, Society of Plastics Engineers, United States 19 pgs.

Compat Yset consisting of four photographs and description, publication date unknown but admitted as prior art, 5 pgs.

Office action issued Feb. 24, 2009 in related U.S. Appl. No. 11/366,226, 17 pgs.

Response filed May 11, 2009 to Office Action dated Feb. 24, 2009 regarding U.S. Appl. No. 11/366,226, 19 pgs.

Office action issued Aug. 24, 2009 in related U.S. Appl. No. 11/366,226, 10 pgs.

* cited by examiner

FIG. 11

| CONDITION # | STATE | IR EMITTER | IR DETECTOR | VISIBLE DETECTOR | STATUS |
|---|---|---|---|---|---|
| 1 | HIGH AMBIENT LIGHT SET NOT LOADED | OFF | ON (ACTIVATED) | ON (ACTIVATED) | FAULT |
| 2 | HIGH AMBIENT LIGHT SET LOADED | ON | ON | OFF | SET LOADED |
| 3 | DARK AMBIENT CONDITION SET NOT LOADED | ON | OFF | OFF | FAULT |
| 4 | DARK AMBIENT CONDITION SET LOADED | ON | ON | OFF | SET LOADED |
| 5 | HIGH AMBIENT LIGHT SET NOT LOADED | ON | ON | ON | FAULT |
| 6 | HIGH AMBIENT LIGHT SET LOADED | OFF | OFF | ON | FAULT |
| 7 | DARK AMBIENT CONDITION SET NOT LOADED | OFF | OFF | OFF | FAULT |
| 8 | DARK AMBIENT CONDITION SET LOADED | OFF | OFF | OFF | FAULT |

FIG. 15

| CONDITION | IR EMITTER | IR DETECTOR | VISIBLE EMITTER | AMBIENT LIGHT | VISIBLE DETECTOR | STATUS |
|---|---|---|---|---|---|---|
| 1 | OFF | OFF | OFF | XX | OFF | FAULT |
| 2 | OFF | OFF | ON | XX | OFF | SET LOADED |
| 3 | OFF | OFF | ON | XX | ON | FAULT |
| 4 | OFF | ON | XX | BRIGHT | XX | FAULT |
| 5 | ON | OFF | XX | XX | XX | FAULT |
| 6 | ON | ON | OFF | XX | OFF | FAULT |
| 7 | ON | ON | OFF | BRIGHT | ON | FAULT |
| 8 | ON | ON | ON | XX | OFF | SET LOADED |
| 9 | ON | ON | ON | XX | ON | FAULT |

FIG. 19

| CONDITION | IR EMITTER | IR DETECTOR | VISIBLE EMITTER | AMBIENT LIGHT | VISIBLE DETECTOR | STATUS |
|---|---|---|---|---|---|---|
| 1 | OFF | OFF | XX | XX | XX | FAULT |
| 2 | ON | OFF | XX | XX | XX | FAULT |
| 3 | ON | ON | OFF | BRIGHT | ON | FAULT |
| 4 | ON | ON | ON | DARK | OFF | SET LOADED |
| 5 | ON | ON | ON | DARK | ON | FAULT |
| 6 | ON | ON | ON | BRIGHT | OFF | SET LOADED |
| 7 | ON | ON | ON | BRIGHT | ON | FAULT |

PUMPING APPARATUS WITH SECURE LOADING FEATURES

CROSS REFERENCE TO RELATED APPLICATION

This application is a continuation of U.S. patent application Ser. No. 11/366,226, filed Mar. 2, 2006, which is hereby incorporated by reference in its entirety.

BACKGROUND OF THE INVENTION

This invention relates generally to pumping apparatus for delivering fluids to patients by way of a flow control apparatus, and more particularly to a pump used with a pump set having a safety interlock device for determining secure loading of the pump set on the pump.

Administering fluids containing medicine or nutrition to a patient is well known in the art. Fluids can be delivered to patients by gravity flow, but often are delivered to the patient by a pump set loaded on a flow control apparatus, such as a peristaltic pump, which delivers fluid to the patient at a controlled rate of delivery. A peristaltic pump usually comprises a housing that includes a rotor or the like operatively engaged to at least one motor through a gearbox. The rotor drives fluid through the tubing of the pump set by the peristaltic action effected by rotation of the rotor by the motor. The motor is operatively connected to a rotatable shaft that drives the rotor, which in turn progressively compresses the tubing and drives the fluid at a controlled rate through the pump set. A controller operates the motor to drive the rotor. Other types of peristaltic pumps not employing rotors are also known.

In order for the pump to deliver an accurate amount of fluid corresponding with the flow parameters programmed into the pump, the administration feeding set must be correctly loaded on the pump. If the pump set is misaligned in the pump, the pump may deliver an inaccurate amount of fluid to a patient or the pump generates a low flow alarm requiring the condition to be examined and the set reloaded. Existing pumps have systems to detect whether the pump set is properly loaded. An example of such a pump having a detection system is shown in co-assigned U.S. Pat. No. 4,913,703, entitled SAFETY INTERLOCK SYSTEM FOR MEDICAL FLUID PUMPS, the disclosure of which is incorporated by reference. This system uses a magnet on the pump set which is detected by circuitry in the pump. It would be desirable to provide a pump set that can be detected but which does not require each pump set to have a magnet.

SUMMARY OF INVENTION

In one aspect of the present invention, a pumping apparatus and pump set are used to deliver a supply of liquid to a patient. The pump set generally comprises a conduit for the liquid and a safety interlock device associated with the conduit. The pumping apparatus generally comprises a pumping device operable to act on the pump set to drive flow of the liquid in the pump set and a control system for controlling operation of the pumping device. At least two sensors are operatively connected to the control system of the pumping apparatus. A first of the sensors is adapted for identifying the safety interlock device in a loaded position of the device and a second of the sensors is adapted for detecting a fault condition associated with positioning of the safety interlock device.

Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

BRIEF DESCRIPTION OF THE DRAWINGS

FIG. 11 is a state diagram of a microprocessor of the pump;
FIG. 15 is a state diagram of a microprocessor of the pump of the ninth embodiment;
FIG. 19 is a state diagram showing conditions encountered in executing the instructions of the software subsystem shown in FIG. 18.

Corresponding reference characters indicate corresponding parts throughout the several views of the drawings.

DETAILED DESCRIPTION

Figure 1:
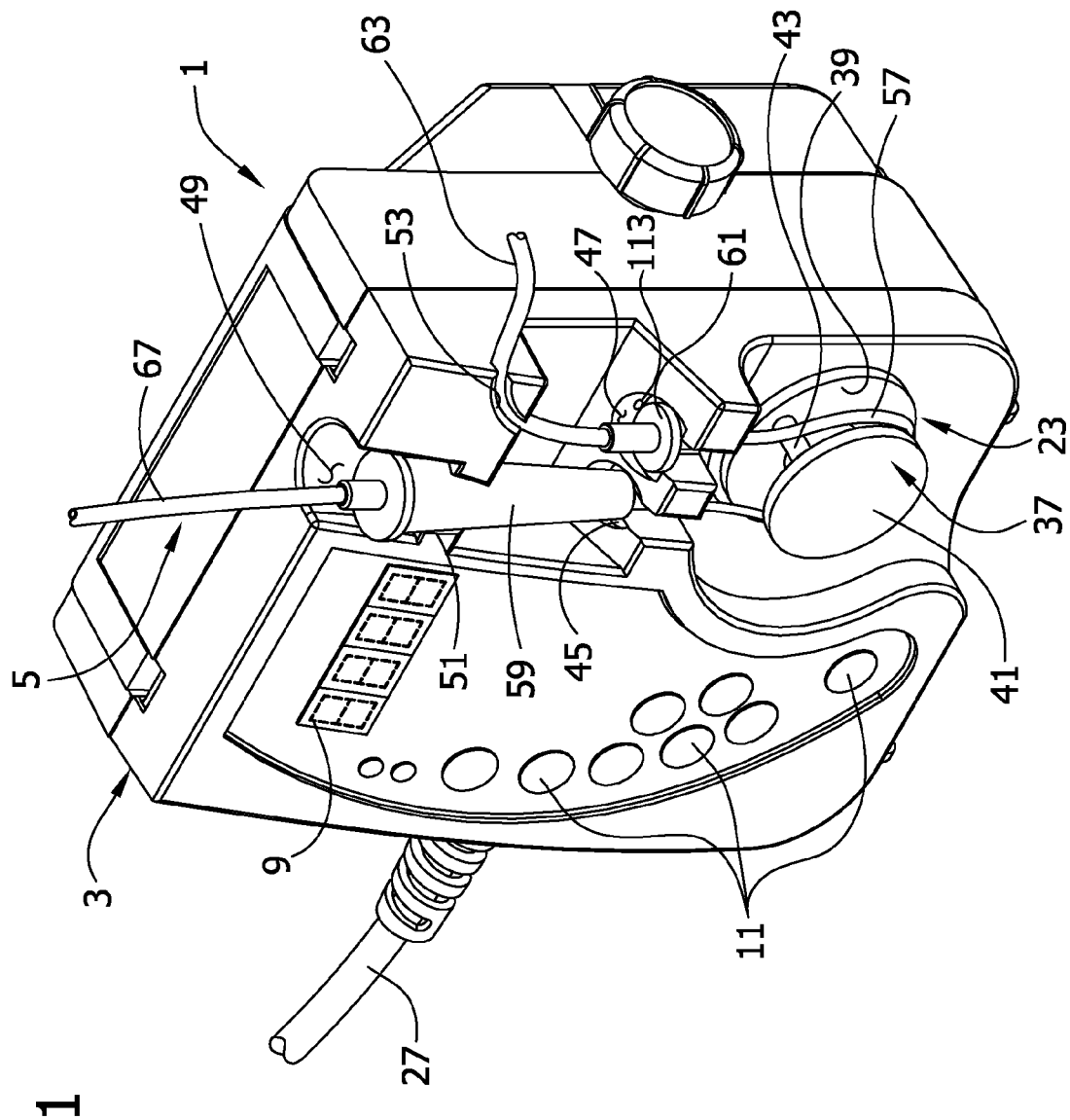
FIG. 1 is a perspective of an enteral feeding pump showing a fragmentary portion of a feeding set received on the pump.
Figure 2:
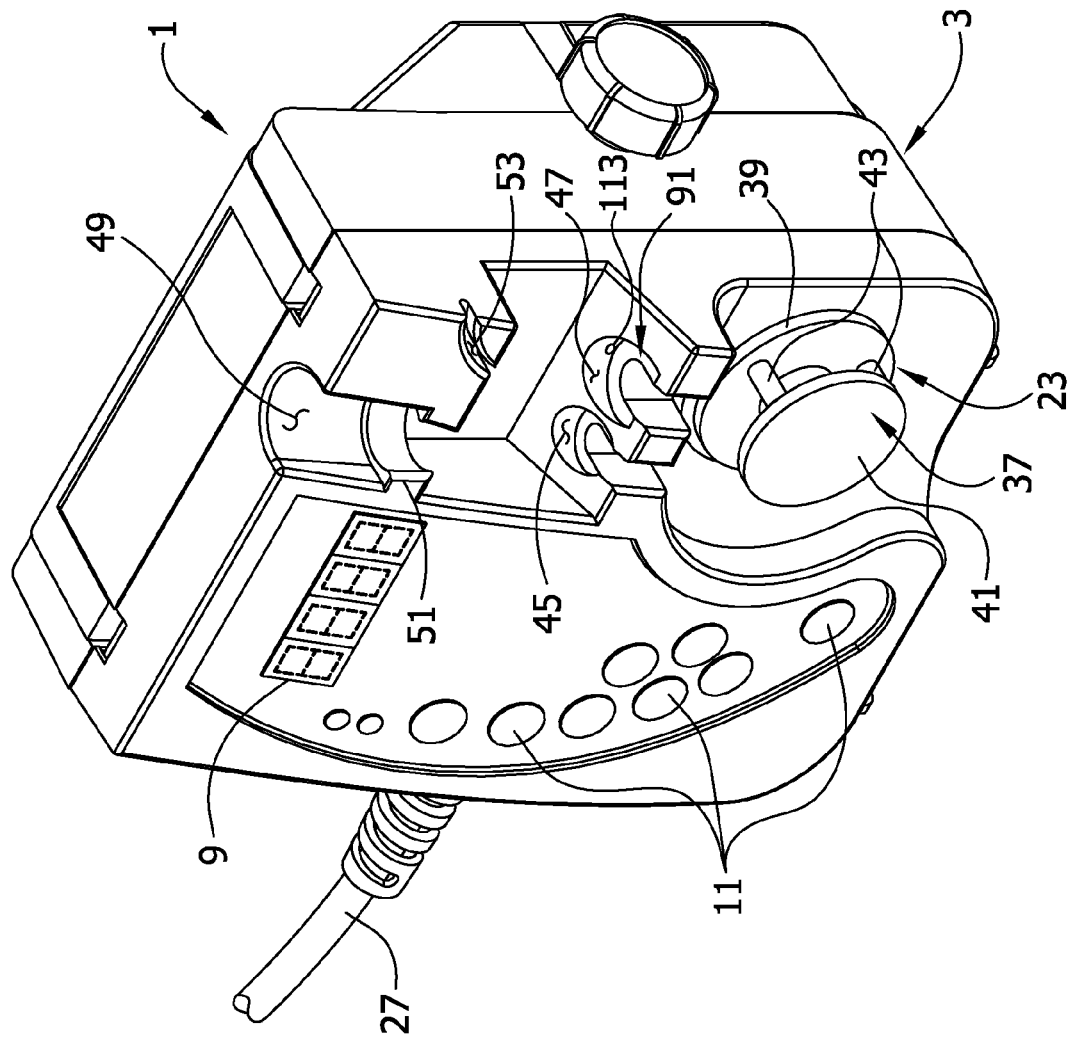
FIG. 2 is a perspective of the pump.

Referring now to the drawings, an enteral feeding pump (broadly, "a pumping apparatus") constructed according to the principles of the present invention is generally indicated at 1. The feeding pump comprises a housing generally indicated at 3 that is constructed so as to mount an administration feeding set (broadly, a "pump set") generally indicated at 5 (see FIGS. 1 and 3). It will be appreciated that "housing" as used herein may include many forms of supporting structures (not shown), including without limitation multi-part structures and structures that do not enclose or house the working components of the pump 1. The pump 1 also has a display screen 9 on the front of the housing 3 that is capable of displaying information about the status and/or operation of the pump. Buttons 11 on the side of the display screen 9 are provided for use in controlling and obtaining information from the pump 1. It will be understood that although the illustrated pump 1 is an enteral feeding pump, the present invention has application to other types of peristaltic pumps (not shown), including medical infusion pumps. A pump of the same general type as described herein is shown in co-assigned U.S. Pat. No. 4,909,797 entitled ENTERAL DELIVERY SET WITH SHADED DRIP CHAMBER, the disclosure of which is incorporated herein by reference.

Figure 4:
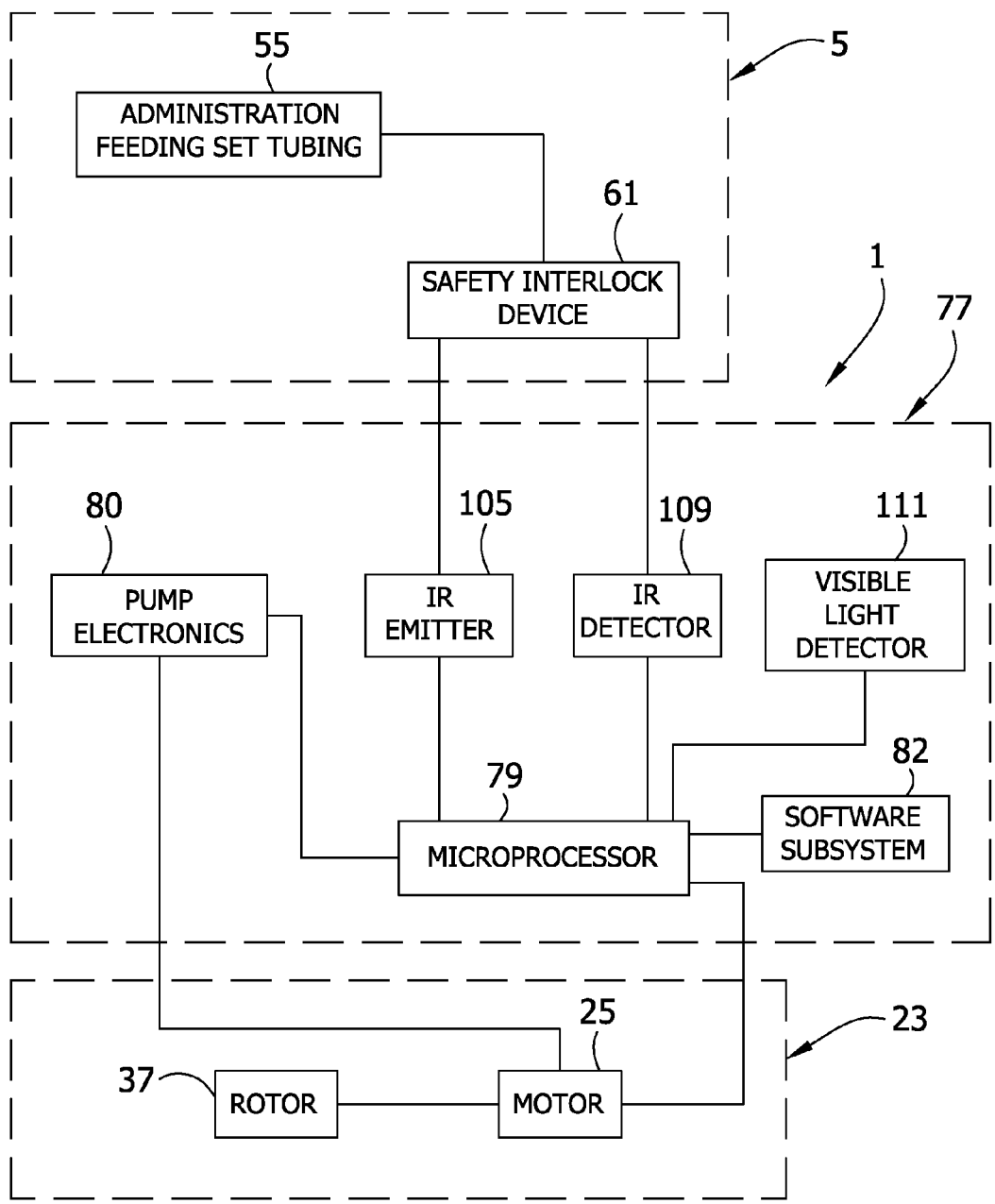
FIG. 4 is a block diagram showing the elements of the pump.

The enteral feeding pump 1 further includes a pumping unit (indicated generally at 23) comprising a pump motor 25 located in the housing 3 and shown schematically in FIG. 4. An electrical cord 27 extends from the housing 3 for connection to a source of electrical power for the motor 25. Alternatively, or in addition, a battery (not shown) may be received in the housing 3 for powering the pump motor 25. The pumping unit 23 further includes a rotor (generally indicated at 37) mounted on a rotor shaft (not shown) of the pumping unit. The rotor 37 includes an inner disk 39, an outer disk 41 and three rollers 43 (only one is shown) mounted between the inner and outer disks for rotation about their longitudinal axes relative to the disks. In the illustrated embodiment, the pump motor 25, rotor shaft and rotor 37 may broadly be considered "a pumping device". The pump housing 3 includes a first lower recess 45 above the rotor 37 and a second lower recess 47 generally adjacent the first lower recess. The housing 3 has an upper recess 49 generally axially aligned with the first lower recess 45 and a shoulder 51 at the bottom of the upper recess for receiving and holding part of the feeding set 5. A curved recess 53 in the housing 3 above the second lower recess 47 receives and holds another part of the administration feeding set 5 in place. The lower recesses 45, 47, upper recess 49 and curved recess 51 may broadly be considered, individually or as a group, "a receiving portion" of the housing 3 that receives parts of the administration feeding set 5 in a manner that will be described in more detail hereinafter.

Figure 3:
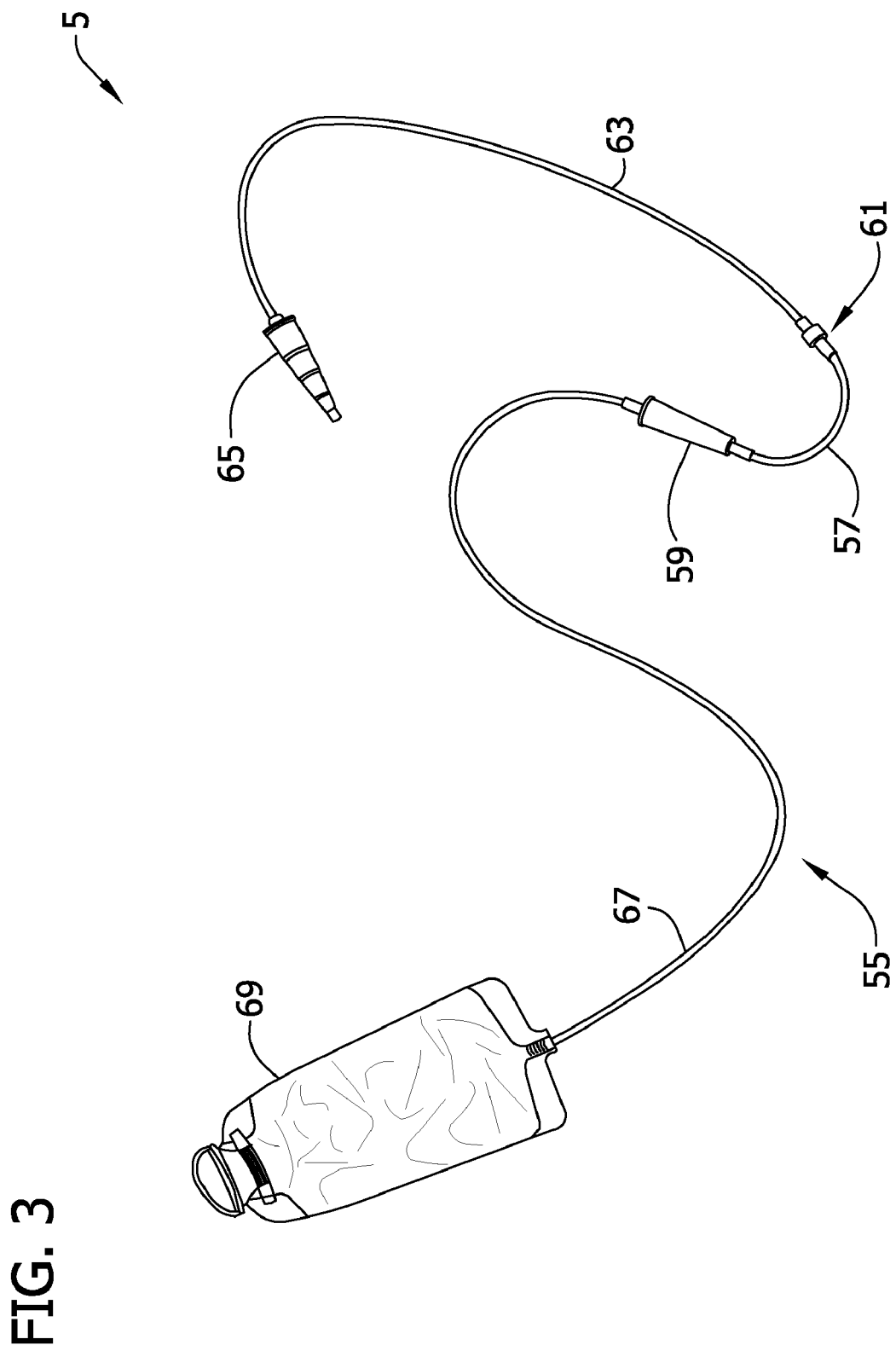
FIG. 3 is an elevation of the administration feeding set.

Referring now to FIG. 3, the administration feeding set 5 comprises tubing (broadly, "a conduit") indicated generally at 55 that provides a fluid pathway between at least one source of fluid and a patient. Tubing 55 can be made of a medical grade, deformable silicone and comprises first tube section 57 connected between a drip chamber 59 and a safety interlock device, generally indicated at 61. A second tube section 63 is connected to the safety interlock device 61 and at an outlet of the tubing 55 to a connector, such as a barbed connector 65, suitable for connection to a gastrostomy device (not shown) attached to a patient. Third tube section 67 is connected at an inlet of the tubing 55 to a bag 69 of nutrient liquid and to the drip chamber 59. As previously stated, pump sets of different constructions may be used, for example a recertification set (not shown) may be used to verify and/or correct the pump accuracy. The pump 1 can be configured to automatically recognize what kind of set is installed and to alter its operation to conform to that called for by the particular pump set. Still further, the pump 1 can be configured to detect with sensors whether the first tube section 57 is properly installed on the pump.

As shown in FIG. 3, the safety interlock device 61 connects first tube section 57 and the second tube section 63 of the administration feeding set 5. The safety interlock device 61 has a central axial bore 81 to allow the flow of fluid between the first tube section 57 and the second tube section 63 (see, FIG. 5). The safety interlock device 61 has an upper cylindrical portion 83 that receives a portion of the tube 57, an electromagnetic radiation propagation affecting member 87 that extends radially outward from the upper cylindrical portion, and a lower cylindrical portion 89 that is received in the second tube section 63 for attaching the second tube section to the safety interlock device. It is to be understood that the safety interlock device 61, and in particular the member 87 may be separate from the administration feeding set 5, and/or may be attached to the administration feeding set in such a way that liquid does not pass through the safety interlock device. The electromagnetic radiation propagation affecting member 87 is sized to be received on a seat, indicated generally at 91, formed at the bottom of the second lower recess 47 in the pump 1 when the administration feeding set 5 is properly loaded on the pump. In the illustrated embodiment, the seat 91 is generally semi-cylindrical to correspond with the shape of the safety interlock device 61 and includes an axially facing surface 95 in the second lower recess 47 and a radially facing surface 99 in the second lower recess 47. In this first and most other embodiments, proper functioning of the pump 1 is generally achieved when the radiation propagation affecting member 87 is seated in substantially face-to-face relation with the axially facing surface 95 of the seat 91. However, the rotation orientation of the member 87, within the seat 91, about its axis is generally not pertinent to operation. In a few embodiments (noted hereinafter) a particular orientation of the member 87 is useful, in which cases keying structures are provided. Other ways of positioning the propagation affecting member 87 may be used within the scope of the present invention. The safety interlock device 61 and the seat 91 in the housing 3 may be shaped to prevent the administration feeding set 5 from being accidentally dislodged and to prevent the use of non-compliant feeding sets that do not have the safety interlock device. In the illustrated embodiment, the safety interlock device 61 and seat 91 are generally cylindrical in shape but it is understood that other shapes (e.g., hex-shaped) may be used for the safety interlock device and the seat. As will be discussed in more detail below, the safety interlock device 61 is comprised of a material (e.g., a thermoplastic polymer resin such as polysulfone thermoplastic resin or other suitable materials) that is opaque to visible light but easily transmits electromagnetic radiation in the infrared range.

Generally speaking, a safety interlock device is able to affect the propagation of electromagnetic radiation by diffusion, diffraction, reflection and/or refraction, or any combination of diffusion, diffraction, reflection and/or refraction. Diffusion is generally understood as the scattering of electromagnetic radiation rays either when reflected from a rough surface or during transmission of electromagnetic radiation through a translucent medium. Diffraction is generally understood as the bending of electromagnetic radiation rays around the edges of opaque objects. Reflection is understood as the return or change in the direction of travel of particles or radiant energy which impinges on a surface but does not enter the substance providing the reflecting surface. Refraction is understood as the change in direction of motion of a ray of radiant energy as it passes obliquely from one medium into another in which the speeds of propagation are different (e.g., media of different densities). The amount of refraction is based on the index of refraction dependent in part on the density of the material facing the medium.

The pump 1 can be programmed or otherwise controlled for operation in a desired manner. For instance, the pump 1 can begin operation to provide feeding fluids from bag 69 to the patient. The care giver may select, for example, the amount of fluid to be delivered, the rate at which the fluid is to be delivered and the frequency of fluid delivery. As shown in FIG. 4, the pump 1 has a controller 77 (broadly, "a control system") including a microprocessor 79 that allows it to accept programming and/or to include pre-programmed operational routines that can be initiated by the care giver. The microprocessor 79 controls pump electronics 80 that operate the motor 25. A software subsystem 82 is used to determine if the feeding set 5 has been positioned properly on the pump 1.

Figure 5:
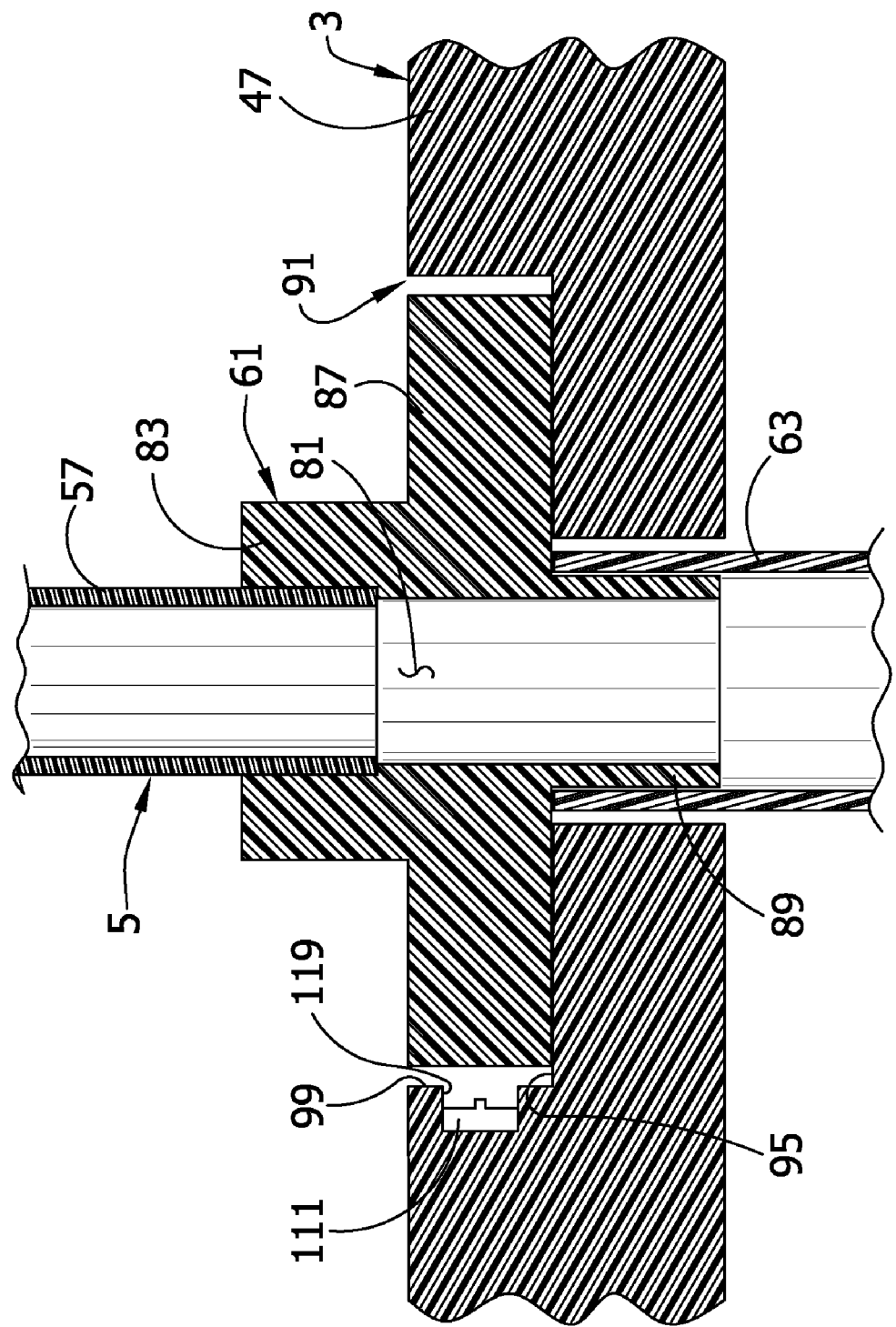
FIG. 5 is an enlarged, fragmentary section of the pump and a safety interlock device of a first embodiment.
Figure 6:
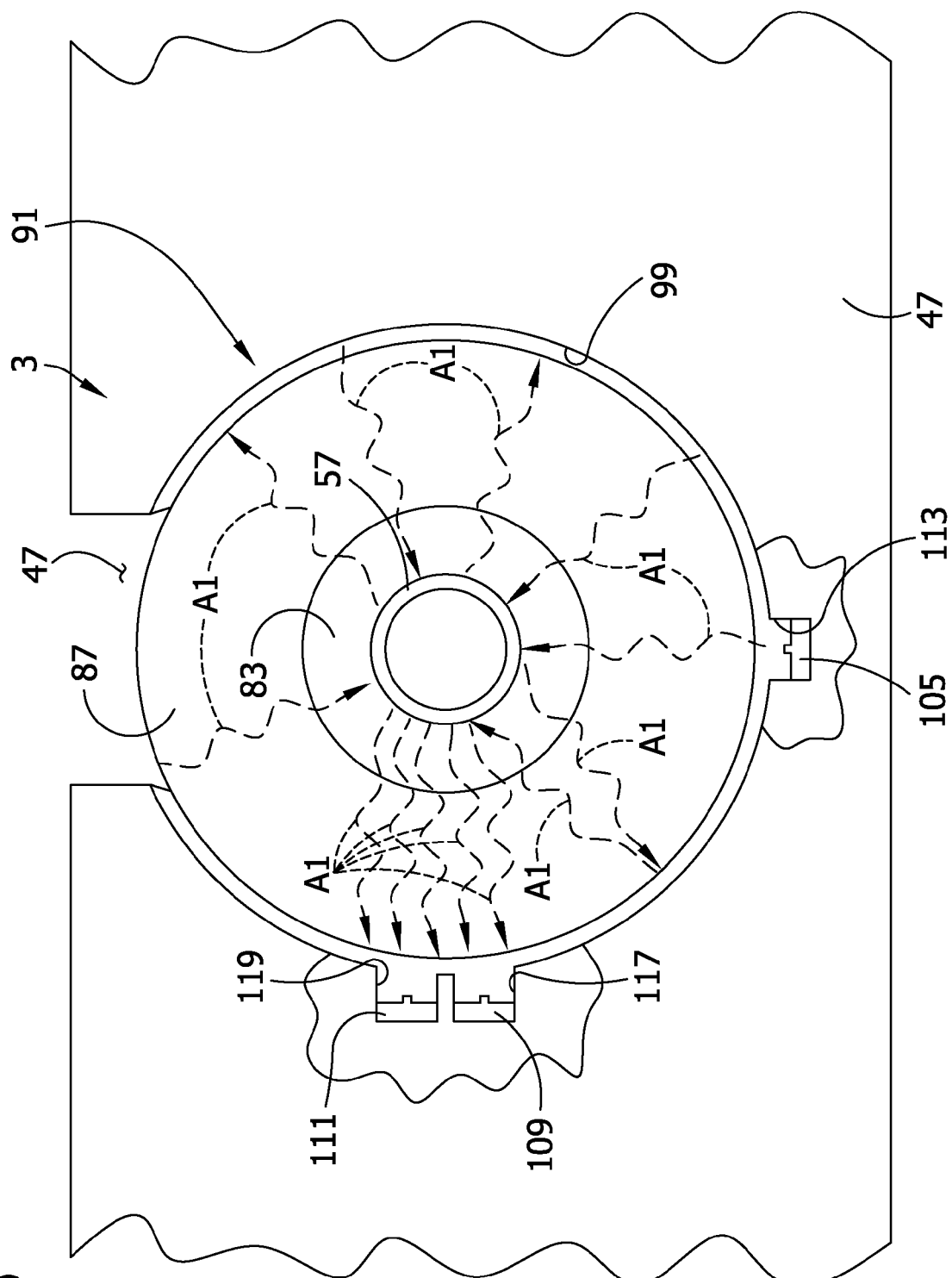
FIG. 6 is a top plan view of FIG. 5.

In the first embodiment, the pump includes an infrared ("IR") emitter 105 (broadly, "a source of electromagnetic radiation") housed in the second lower recess 47. Referring to FIGS. 5 and 6, the IR emitter 105 is operatively connected to the controller 77 for emitting an electromagnetic signal having a ("first") wavelength in the infrared range in a direction for striking the safety interlock device 61 of the feeding set 5. In the illustrated embodiment, the source of electromagnetic radiation is an infrared (IR) emitter 105 but it is understood that other types of sources of electromagnetic radiation may be used without departing from the scope of this invention. An infrared ("IR") detector 109 located in the second lower recess 47 is operatively connected to the controller 77 for receiving the infrared signal from the IR emitter 105 and providing an indication to the controller that the feeding set 5 is properly positioned in the pump 1. In the illustrated embodiment, the IR detector 109 (broadly, "a first sensor") detects infrared radiation but it is understood that electromagnetic radiation sensors that detect other types of electromagnetic radiation may be used without departing from the scope of this invention. The IR detector 109 distinguishes infrared radiation from other types of electromagnetic radiation (e.g., visible or ultraviolet light). A visible light detector 111 (broadly, "a second electromagnetic radiation detector" and "a second sensor") is housed in the second lower recess 47 generally adjacent the IR detector 109. The visible light detector 111 provides a signal to the controller 77 when visible light from the surrounding environment (e.g., electromagnetic radiation of a second wavelength) is detected to indicate that the safety interlock device 61 is not mounted in the second lower recess 47 in a position that blocks visible light from reaching the detector. Preferably, the visible light detector 111 is configured to detect electromagnetic radiation in the visible range, but not to detect electromagnetic radiation outside the visible range (e.g., infrared radiation). A second electromagnetic radiation detector could be configured to detect electromagnetic radiation in other ranges, such as in the ultraviolet range. Thus, the visible light detector 111 can distinguish visible light from infrared radiation. As used herein, electromagnetic radiation of a "first" or "second" wavelength is intended in each case to encompass a range of wavelengths, such as wavelengths falling in the infrared range, visible range and/or ultraviolet range.

Other sensors (not shown), such as a sensor that determines the type of pump set that has been placed in the pump 1 and a flow monitoring sensor can be in communication with the controller 77 to facilitate accurate operation of the pump. The IR emitter 105 is positioned in an alcove 113 in the second lower recess 47 of the housing 3 so that electromagnetic radiation (indicated by arrows A1 in FIG. 6) from the emitter is directed to the electromagnetic radiation propagation affecting member 87 of the safety interlock device 61 (see also, FIG. 5). When the safety interlock device 61 is properly located on the seat 91, the infrared radiation from the IR emitter 105 is diffused through the electromagnetic radiation propagation affecting member 87 and internally reflected so that the infrared radiation is directed to and detected by the IR detector 109. Diffusion may be enhanced by the addition of particulates to the material of the member 87. In this first embodiment (and other embodiments) the infrared radiation propagation is affected primarily through internal reflection. Other effects on infrared radiation propagation, such as diffusion, may also assist. However, any infrared radiation that is refracted is minimal and does not contribute to the infrared radiation signal seen by the IR detector 109 (i.e., refraction causes a reduction in signal strength). The IR detector is positioned in an alcove 117 in the radially facing surface 99 of the seat 91 and the visible light detector 111 is positioned in an alcove 119. The alcoves 113, 117, 119 recess the IR emitter 105 and the IR and visible light detectors 109, 111 to protect them from physical contact with the propagation affecting member 87. Although not shown, a clear plastic window may enclose each of the emitter 105 and the detectors 109, 111 within their corresponding alcoves 113, 117, 119 for additional protection. Moreover, the alcoves 117 and 119 help to shield the detectors 109 and 111 from ambient electromagnetic radiation (which may include both visible light and infrared radiation).

In the illustrated first embodiment, the IR emitter 105 is located approximately 90 degrees from the IR detector 109. When the feeding set 5 is not loaded in the second lower recess 47 and the electromagnetic radiation propagation affecting member 87 is not received on the seat 91, the infrared radiation from the IR emitter 105 is not detected by the IR detector 109. Also when the safety interlock device 61 is not received on the seat 91, visible light from outside of the pump 1 (i.e., ambient light) may enter the second lower recess 47 and is detected by the visible light detector 111. The propagation affecting member 87 is preferably constructed of a material that transmits infrared radiation, but is opaque to visible light. The propagation affecting member 87 may be monolithic or may have other constructions such as an outer layer (not shown) that transmits infrared radiation, but does not transmit visible light and an inner layer or core that is transmissive to both infrared radiation and visible electromagnetic radiation.

Figure 6A:
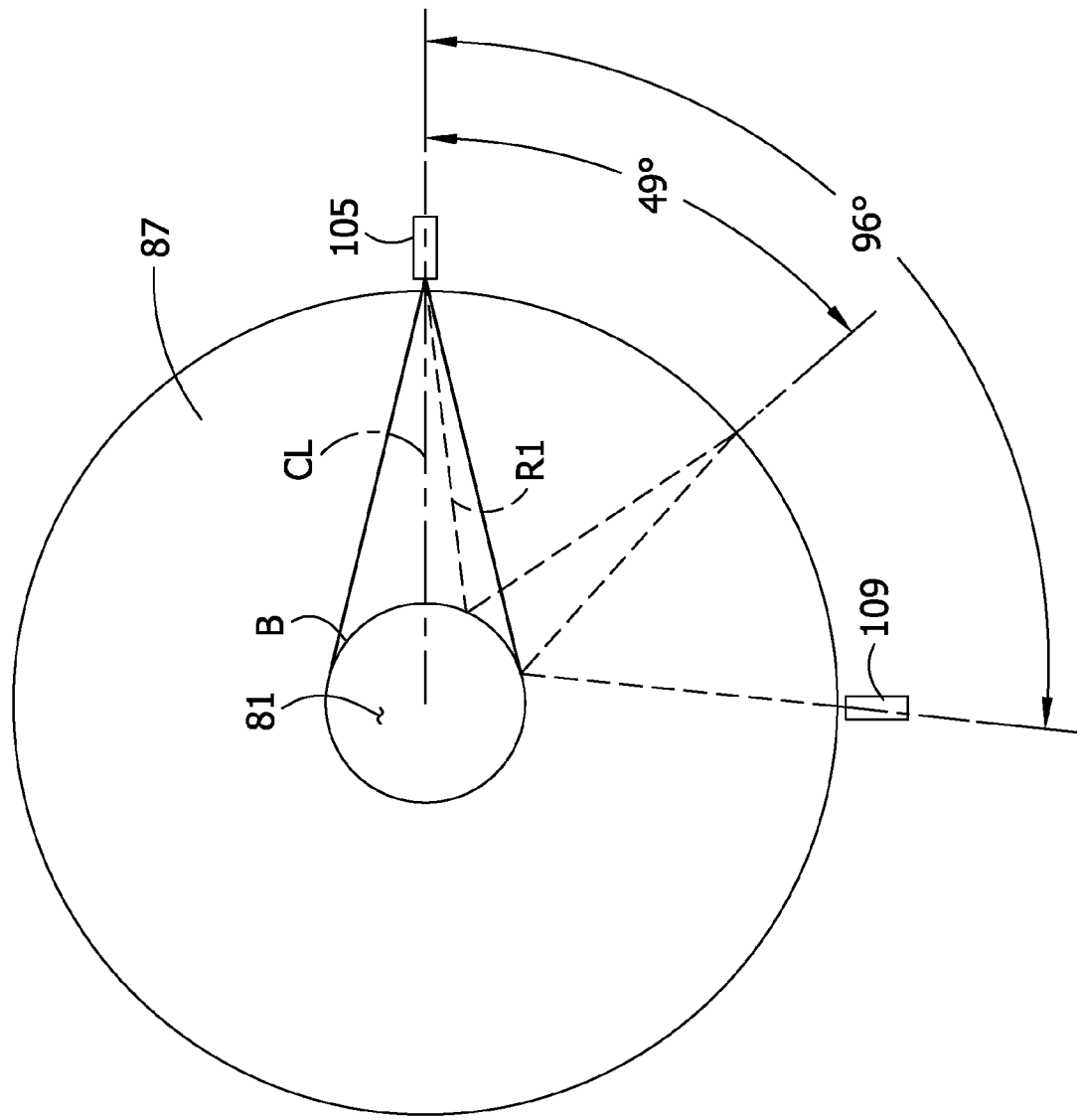
FIG. 6A is a schematic diagram similar to FIG. 6 showing propagation of a light ray in the safety interlock device.

Referring now to FIG. 6A, movement of infrared radiation within the electromagnetic radiation propagation affecting member 87 is schematically illustrated. The IR emitter 105 emits infrared radiation in a cone toward the side of the member 87. The IR emitter 105 is arranged generally perpendicular to the immediately adjacent side of the member 87. The centerline CL of the cone is denoted in the drawing. For simplicity, we will ignore diffusion and look at a ray R1 of radiation that is a bisector of approximately one half of the cone. The ray R1 is representative of the nominal path of infrared radiation in this half of the cone. The other half of the cone (i.e., that portion above the centerline CL in FIG. 6A) is believed to be of small or no use in providing a light signal capable of being detected by the IR detector 109. The ray R1 strikes the side of the propagation affecting member 87 at an angle so that it enters the member rather than being reflected back. The ray R1 travels generally toward the center of the member 87 until it reaches a boundary B (broadly, "an inner boundary region") around the axial bore 81 of the member. The ray R1 is reflected back toward the side of the member 87 where a good percentage of the ray is reflected back toward the center. At the boundary B, the ray R1 is once more reflected back toward the side of the member 87. Finally, the ray strikes the interior side of the member 87 at a location that is about 96 degrees away from the location of the IR emitter 105. It has been found that a particularly high level of intensity of infrared radiation escapes the member 87 at this location. Accordingly, the IR detector 109 is preferably positioned here, or in a range of around 75-105 degrees. Another higher intensity node is found at a location around 49 degrees from the IR emitter 105, as would be expected from the reflection.

The boundary B of the electromagnetic radiation propagation affecting member 87 can be made of the same material as the remainder of the member. The material at the boundary B may be more "polished" (i.e., more specular) than elsewhere to increase its ability to reflect electromagnetic radiation impinging upon the boundary. However, it is also possible that the central part of the member 87 could be formed of a separate material. In that case, the member 87 would be formed of an inner and an outer member, such as described below in regard to FIG. 22. In use, the administration feeding set feeding fluid bag 69 can be hung from a suitable support, such as an IV pole (not shown). The drip chamber 59 can be placed in the first lower recess 45 and upper recess 49 in an operating position as shown in FIG. 1. The first tube section 57 is placed around the lower part of the rotor 37 and the safety interlock device 61 is placed on the seat 91 at the bottom of the second lower recess 47. The seat 91 in the second lower recess 47 is generally located so that the safety interlock device 61 can be placed into the second lower recess at a location in which the first tube section 57 is substantially stretched around the rotor 37. The IR emitter 105 and IR detector 109 may intermittently or continuously check for the presence of the properly loaded feeding set 5. When the safety interlock device 61 is received in a proper operating position on the seat 91, the infrared signal from the IR emitter 105 is directed to the electromagnetic radiation propagation affecting member 87. The electromagnetic radiation propagation affecting member admits the infrared radiation into its interior where the electromagnetic radiation is diffused and internally reflected (see FIGS. 6 and 6A). Some of the infrared radiation which is redirected outward and impinges the outer boundary of the electromagnetic radiation propagation affecting member 87 substantially at right angles thereto passes out of the electromagnetic radiation propagation affecting member. Some of the escaping infrared radiation is directed toward the IR detector 109. The IR detector is periodically operated and detects the presence of infrared radiation when the feeding set 5 has been properly loaded on the pump. It is understood that the IR detector 109 is preferably unable to detect electromagnetic radiation having a wavelength in the visible light region of the electromagnetic spectrum. Upon detection of the infrared signal, the IR detector 109 sends a corresponding signal to the microprocessor 79. Also, when the safety interlock device 61 is loaded onto the seat 91, visible light is blocked by the member 87 from reaching the visible light detector 111. When the set 5 is loaded, the visible light detector 111 sends a signal to the microprocessor 79 to indicate that visible light is blocked and the pump 1 may be operated.

In one embodiment, the IR emitter 105 and IR detector 109 are both operated intermittently to detect the presence of the safety interlock device 61 on the seat 91. The IR emitter 105 is operated to generate a pattern of infrared radiation pulses. The IR detector 109 is operated in a series of detector activations or pulses that check for the presence of electromagnetic radiation from the IR emitter 105. Typically, the number of activations from the IR detector 109 will be greater than the number of pulses from the IR emitter 105 for a given period of time. For example, the IR detector 109 may have two activations in a three second time period and the IR emitter 105 may be programmed to generate one pulse of infrared radiation during the three second time period. During the three second time period, the pump 1 has a ratio of detector activations to emitter activations of about 2:1. It is understood that the pump 1 may have other ratios and that the IR emitter 105 and IR detector 109 may operate in other predetermined intermittent patterns without departing from the scope of this invention. The IR detector 109 and the controller 77 may be configured for recognizing a particular, and for example irregular, pattern of activations of the IR emitter 105.

Figure 7:
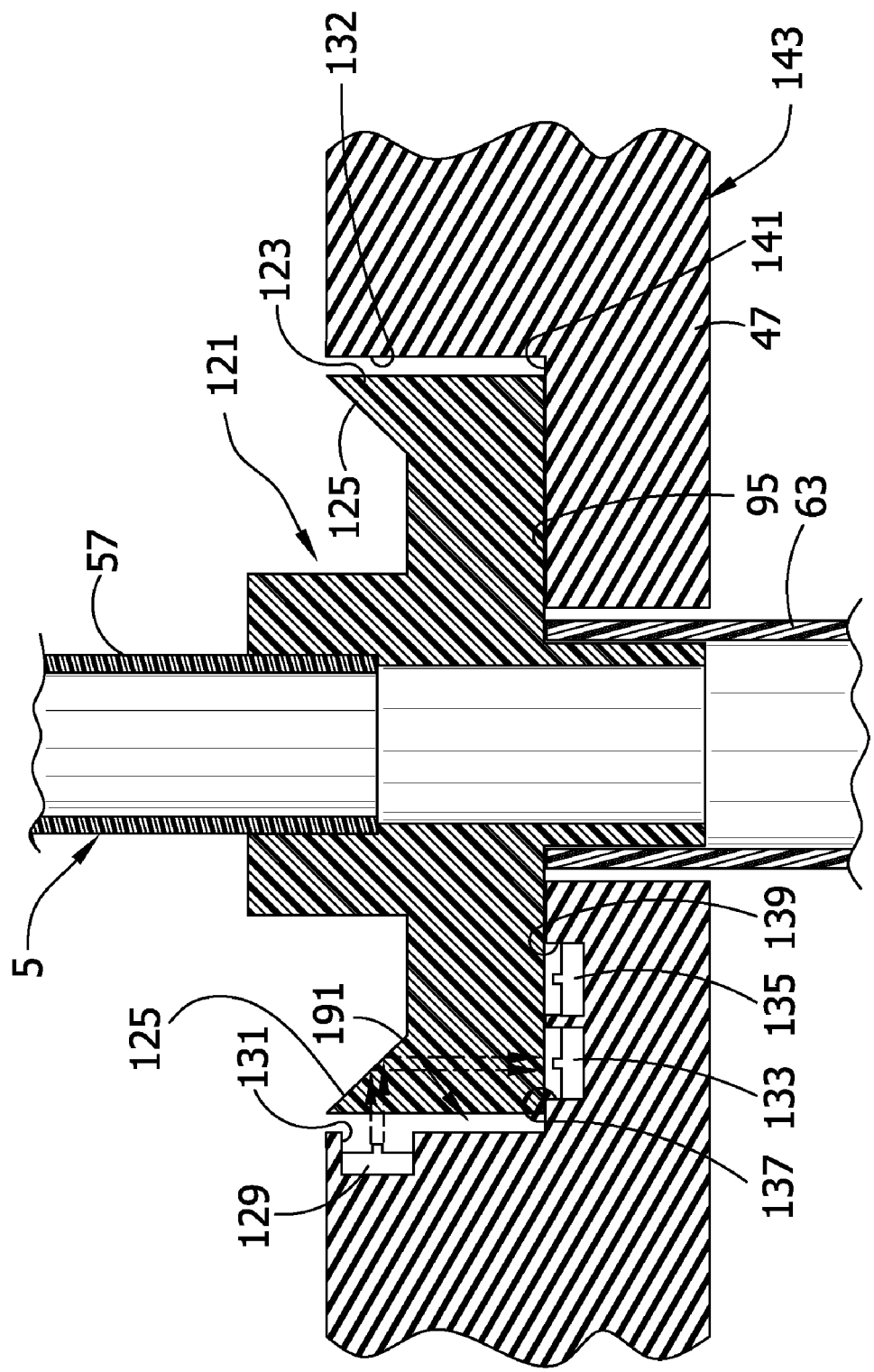
FIG. 7 is an enlarged, fragmentary section of a pump and safety interlock device of a second embodiment.

FIG. 7 shows a seat 191 and a safety interlock device 121 of a second embodiment of the present invention. The safety interlock device 121 of this embodiment has a electromagnetic radiation propagation affecting member 123 with an angled annular surface 125. The IR emitter 129 is located in an alcove 131 in a radially facing surface 132 of a seat 191 of housing 143 and is positioned to direct infrared radiation toward the safety interlock device 121 in a similar manner as the first embodiment. In the embodiment of FIG. 7, the IR detector 133 and visible light detector 135 are located in respective alcoves 137, 139 in an axially facing surface 141 of the seat 191. The angled annular surface 125 is reflective so that it reflects infrared radiation from the IR emitter 129 downward to the IR detector 133 when the safety interlock device 121 is received on the seat 191 of the housing 143. When the safety interlock device 121 is not properly received in the seat 191, visible ambient light can be detected by the visible light detector 135.

Figure 7A:
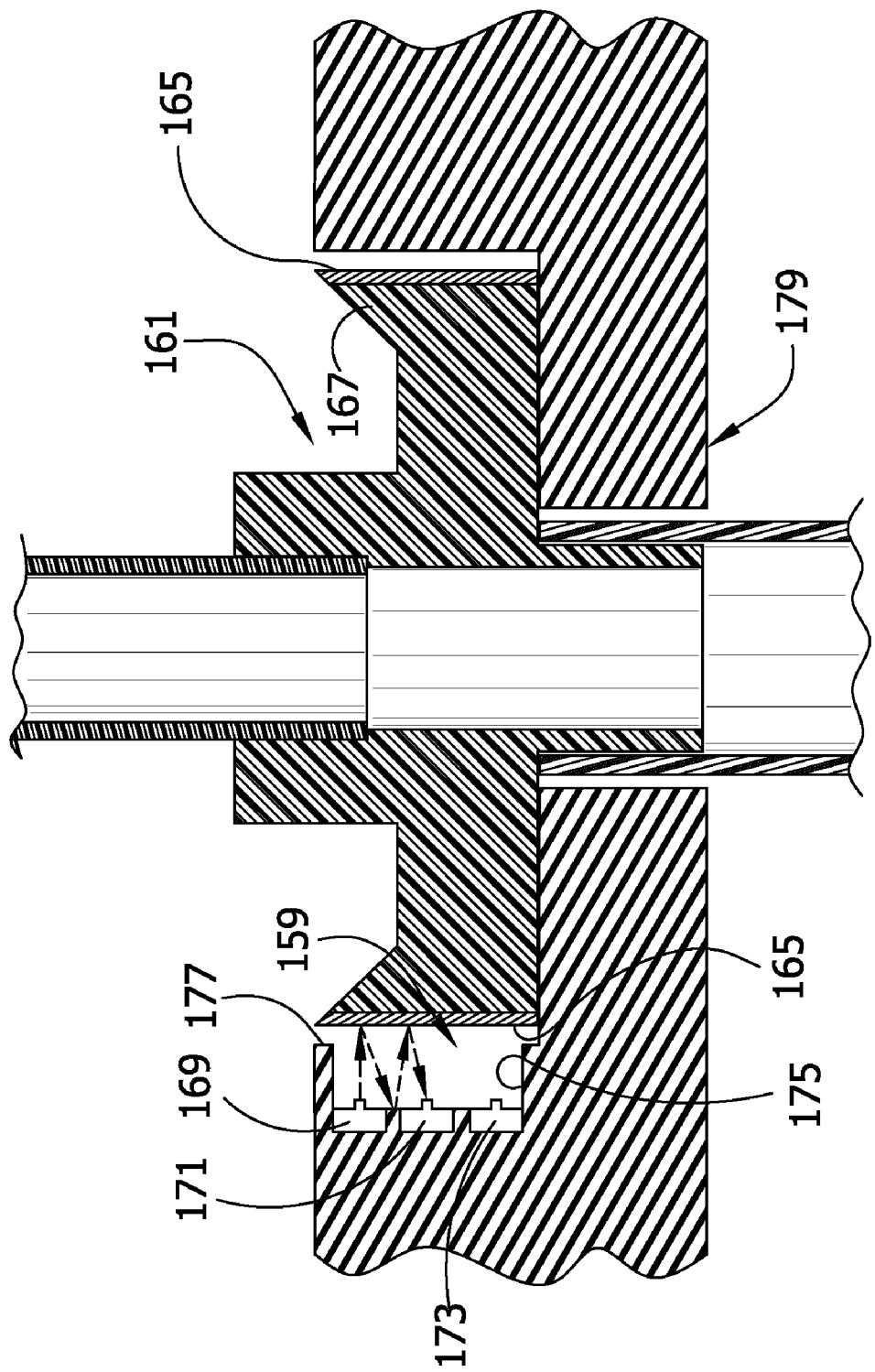
FIG. 7A is an enlarged, fragmentary section of a pump and a safety interlock device of a third embodiment.

FIG. 7A shows a seat 159 and a safety interlock device 161 of a third embodiment of the present invention. In this embodiment, the safety interlock device 161 includes a reflector 165 on the external radial surface of an electromagnetic radiation propagation affecting member 167. The reflector 165 may be a layer of reflective tape or a layer of polished metal affixed to the remainder of the electromagnetic radiation propagation affecting member 167. In the embodiment of FIG. 7A, the IR emitter 169, the IR detector 171, and the visible light detector 173 are arranged in an alcove 175 in a radially facing surface 177 of housing 179 in a manner such that the three devices are generally vertically aligned and parallel to each other. It is understood the IR emitter 169, IR detector 171, and visible light detector 173 may be otherwise arranged. When the safety interlock device 161 is received in the seat 159, the infrared radiation emitted from the IR emitter 169 is reflected off the reflector 165 and transmitted to the IR detector 171 and ambient visible light is blocked from detection by the visible light detector 173. When the safety interlock device 161 is not loaded in the seat 159, infrared radiation is not transmitted to the IR detector 171 and ambient visible light can be detected by the visible light detector 173.

Figure 8:
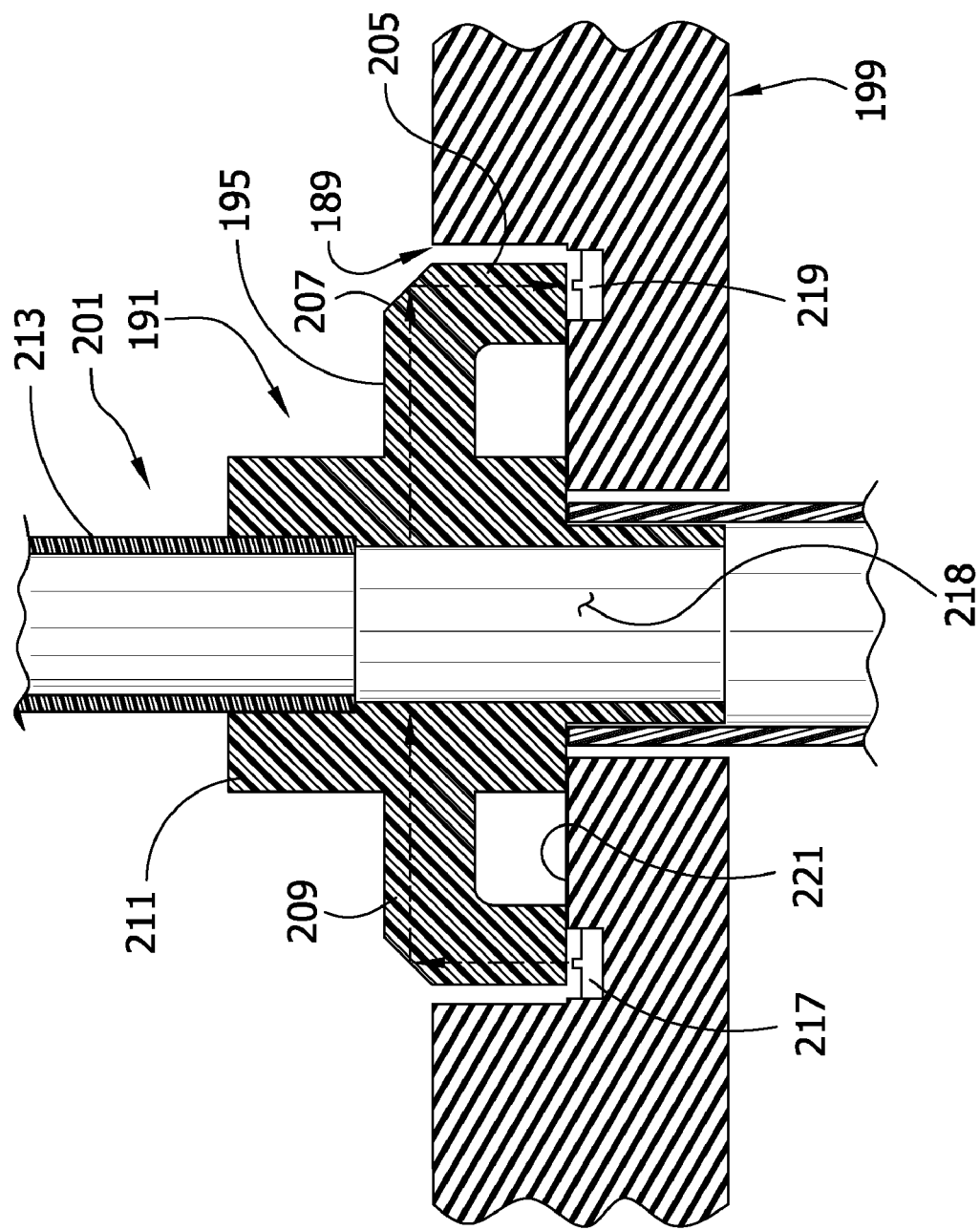
FIG. 8 is an enlarged, fragmentary section of a pump and a safety interlock device of a fourth embodiment.

FIG. 8 shows a seat 189 and safety interlock device 191 of a fourth embodiment of the present invention. As in the prior embodiments, the safety interlock device 191 can be removably positioned on the seat 191 and thereby releasably attached to the pump by the user or caregiver. In this embodiment, the safety interlock device 191 includes a light pipe 195 ("an electromagnetic radiation propagation affecting member") received in the seat 189 of the housing 199 when the feeding set 201 is loaded on the pump. The light pipe 195 includes an outer annular portion 205, an angled annular wall 207, and a central portion 209 between the angled wall and the upper portion 211 that receives a tube 213 of the feeding set 201. As shown in FIG. 8, the IR emitter 217 and IR detector 219 are both housed below a bottom wall 221 of the seat 189.

The IR emitter 217 directs infrared radiation upward to the outer annular portion 205 of the light pipe 195 that is reflected by the angled annular wall 207 through the central portion 209 of the light pipe (around a central fluid passage 218) before being reflected to the IR detector 219 by the angled annular wall 207 on the opposite side of the light pipe. When the safety interlock device 191 is not properly seated on the seat 189 in the loaded position of the feeding set 201, the IR signal from the IR emitter 217 is not transmitted through the light pipe 195 to the IR detector 219. A visible light detector (not shown) may be present for use in detecting ambient light as in earlier embodiments of the invention.

Figure 9:
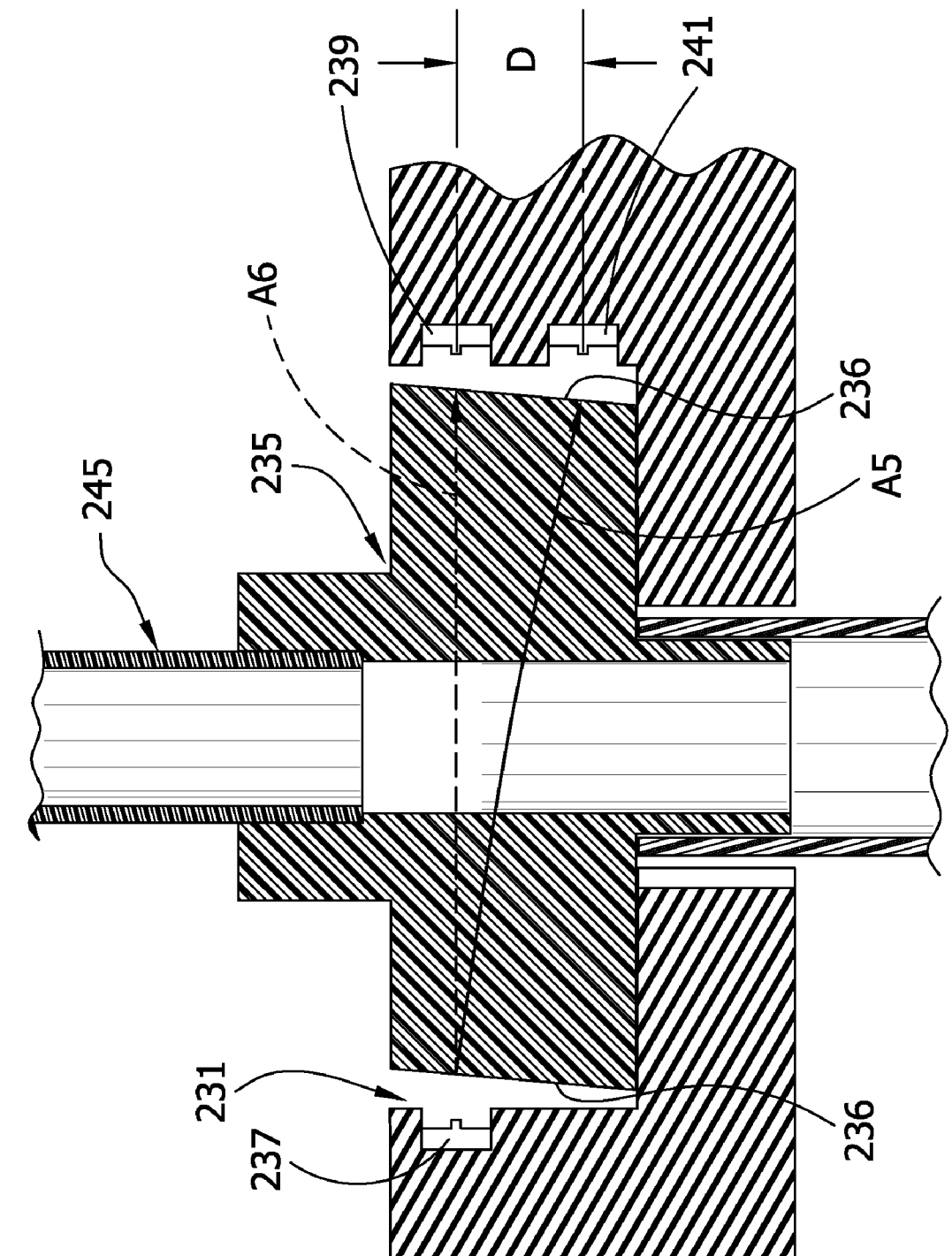
FIG. 9 is an enlarged, fragmentary section of a pump and a safety interlock device of a fifth embodiment.

FIG. 9 shows a seat 231 and a safety interlock device 235 of a fifth embodiment of the present invention. This safety interlock device 235 of this embodiment comprises an infrared radiation transmissive material that also refracts the infrared radiation transmitted through the safety interlock device. The safety interlock device 235 has a generally polygonal shape. Opposite sides 236 of the safety interlock device 235 are angled parallel to each other. The seat 231 is keyed to receive the safety interlock device in the particular orientation illustrated in FIG. 9 so that electromagnetic radiation is refracted in the desired manner, as will be described. An IR emitter 237, an upper IR detector 239 (broadly, "a second detector"), and a lower IR detector 241 (broadly, "a first detector") are positioned for sensing if an administration feeding set 245 has been properly loaded into the pump. The upper and lower IR detectors 239, 241 are positioned on the opposite side of the seat 231 from the IR emitter 237 such that the emitter and the detectors are oriented at approximately 180 degrees with respect to each other. Also, the upper IR detector 239 and lower IR detector 241 are spaced apart a distance D so that when infrared radiation is passed through the safety interlock device 235, the radiation (as indicated at arrow A5) is refracted or bent downward so that the lower IR detector 241 senses the presence of infrared radiation and sends a signal to the microprocessor to enable operation of the pump. The sides of the safety interlock device 25 are angled parallel to each other so that refraction of the infrared radiation is directed by the refraction to the lower IR detector 241. When the safety interlock device 235 is not loaded in the seat 231 of the pump, the infrared radiation from the IR emitter 237 (as indicated by phantom arrow A6) passes through the seat such that the beam of infrared radiation is directed to only the upper IR detector 239, which sends a signal to the controller to disable operation of the pump. The density and width of the safety interlock device 235 affects the distance D between the upper detector 239 and the lower detector 241 so that if an feeding set is used having a safety interlock device made of a material having a different density and/or width, the electromagnetic radiation will not be refracted the proper distance to impinge on the lower IR detector 241 even if the feeding set is properly loaded. A visible light detector (not shown) may be present for use in detecting ambient light as in earlier embodiments of the invention.

Figure 10:
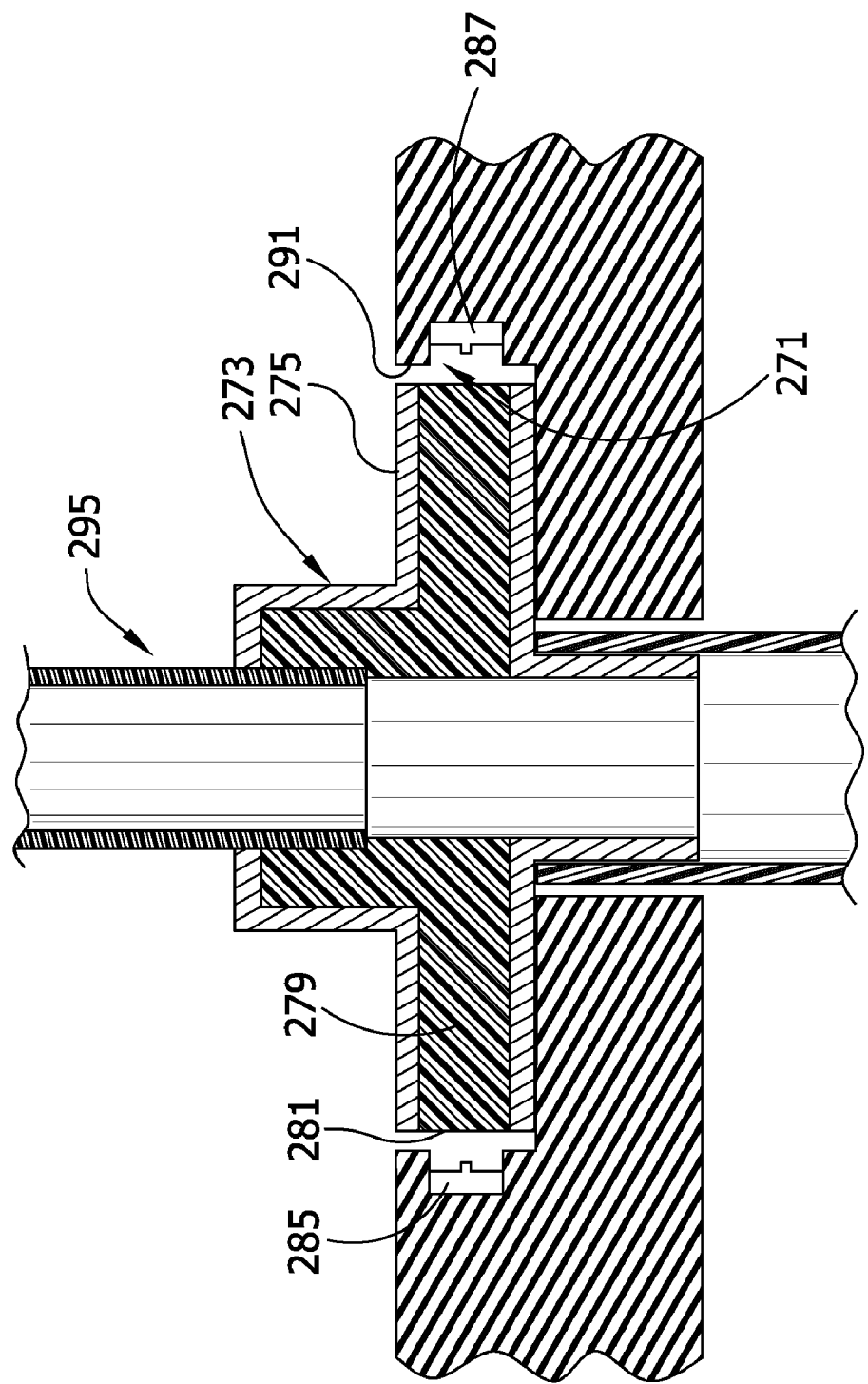
FIG. 10 is an enlarged, fragmentary section of a pump and a safety interlock device of a sixth embodiment.

FIG. 10 shows a seat 271 and safety interlock device 273 of a sixth embodiment of the present invention. The safety interlock device 273 of this embodiment is generally similar to the first embodiment but includes a layer 275 of infrared radiation blocking material on the external surface of the safety interlock device. As in the first embodiment, the safety interlock device 273 includes an electromagnetic radiation propagation affecting member 279 that transmits infrared radiation through the safety interlock device. The external radial surface 281 of the electromagnetic radiation propagation affecting member 279 is free from infrared radiation blocking material as this surface is used to receive the infrared signal from the IR emitter 285 so that the IR signal is transmitted through the safety interlock device 273 for detection by the IR detector 287. It is understood that the IR emitter 285 and IR detector 287 of this embodiment may be positioned at any angle around the radial surface 291 of the seat 271. The IR blocking layer 275 prevents infrared electromagnetic radiation from outside sources (e.g., sunlight) from reaching the IR detector 287 when the administration feeding set 295 is loaded on the pump. It is envisioned that portions of the radial surface 281 of the electromagnetic radiation propagation affecting member 279 may have IR blocking material thereon. In that event, the electromagnetic radiation propagation affecting member 279 is preferably keyed with structure (not shown) on the seat 271 so that the IR emitter 285 and IR detector 287 are unblocked. A visible light detector (not shown) may be present for use in detecting ambient light as in earlier embodiments of the invention.

The safety interlock device 273 of this embodiment may be constructed by a "co-injection molding" process also referred to as a "two-shot injection molding" process. The process includes injection molding the safety interlock device 273 with the electromagnetic radiation propagation affecting member 279 comprising an infrared radiation transmissive material (e.g., light transmissive thermoplastic polymer resin) together with the IR blocking layer 275 (e.g., an opaque thermoplastic polymer resin). Other variations of this embodiment may include the use of a visible light blocking material (e.g., thermoplastic polymer resin mixed with red dye) instead of an IR blocking material to allow infrared electromagnetic radiation to pass through the safety interlock device but prevent visible light from passing through the device.

FIG. 11 is a state diagram illustrating the various conditions the controller 77 (FIG. 4) may encounter when operating the software subsystem 82 to determine if the safety interlock device 61 is properly loaded on the pump. The state diagram has application to other embodiments, but will be described in respect to the first embodiment. As shown in FIG. 11, for the controller to provide a "SET LOADED" status, the status of the IR emitter 105 and IR detector 109 must be "ON" and the status of the visible light detector 111 must be "OFF". Any other combination of status indications from the IR emitter 105, IR detector 109 and visible light detector 111 results in a "FAULT" status being indicated by the controller. The "FAULT" status will prompt the user to check the loading of the safety interlock device 61 and will prevent the pump 1 from operating. Once the feeding set 5 is properly loaded, the controller 77 will sense a "SET LOADED" condition and initiate operation of the pump 1. During operation of the pump, the IR emitter 105 may operate continuously so that the safety interlock status is continuously monitored and if the status changes from "SET LOADED" to "FAULT", the controller 77 will stop operating the pump 1 and enter an alarm condition. Optionally, the IR emitter 105 may be operated intermittently with brief pulses of infrared electromagnetic radiation being transmitted at a set time interval to the IR detector 109 so that the safety interlock status is continuously monitored. The visible light detector 111 may continuously check for the presence of visible light so that if the safety interlock 61 is removed from the seat 91 and allows visible light into the recess, the visible light detector 111 immediately senses this condition and signals the controller 77 to enter an alarm condition. The visible light detector 111 may operate intermittently without departing from the scope of this invention.

Figure 12:
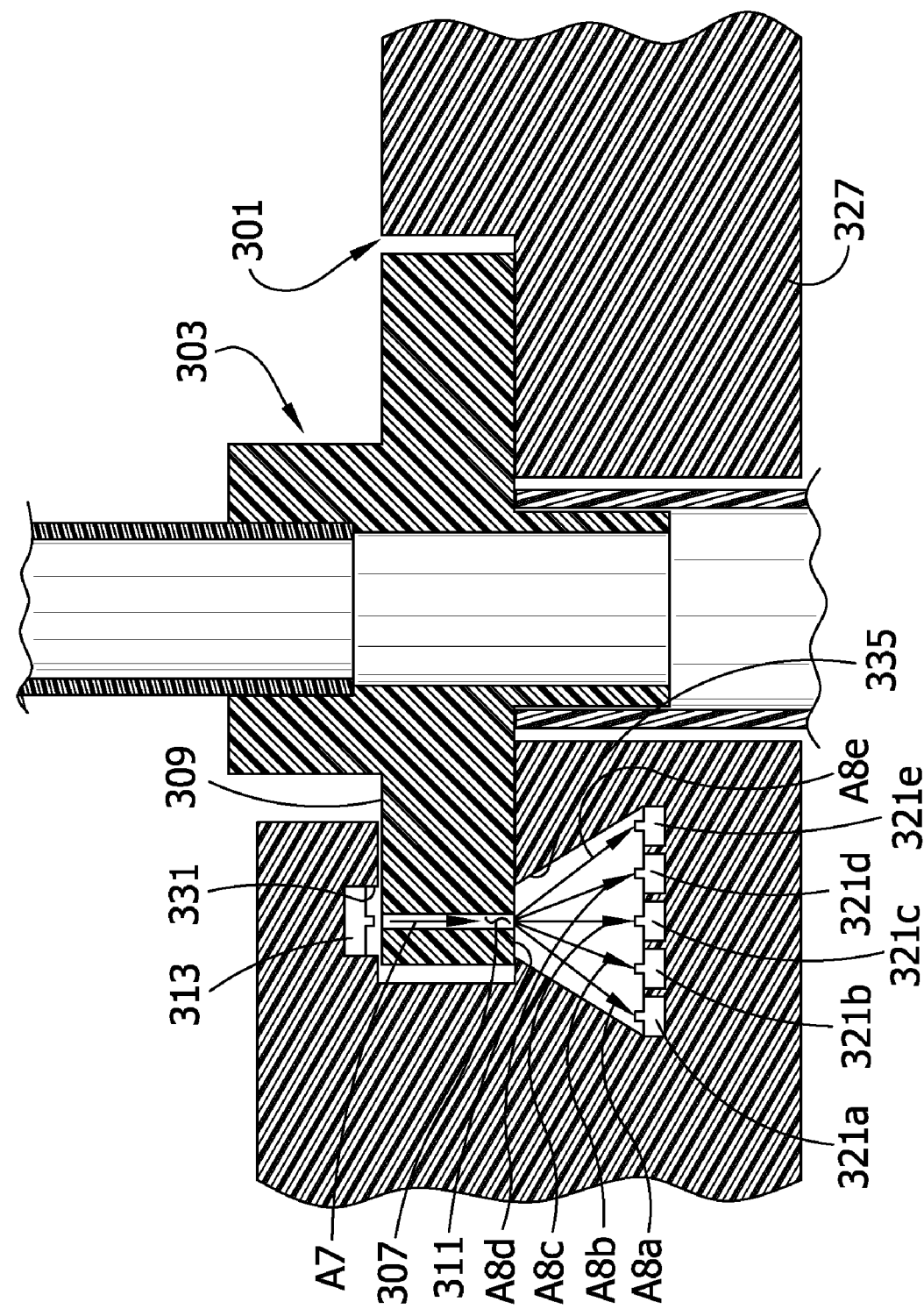
FIG. 12 is a an enlarged, fragmentary section of a pump and a safety interlock device of a seventh embodiment.

FIG. 12 shows a seat 301 and safety interlock device 303 of a seventh embodiment of the present invention. In this embodiment, the safety interlock device 303 is made of an infrared radiation opaque material and has an opening 307 passing from the top surface 309 to the bottom surface 311 of the device. The opening 307 is configured to break the beam of infrared radiation (indicated at A7) from the IR emitter 313 via diffraction into a series of spaced apart beams (indicated at A8a thru A8e) that are detected by a series of IR detectors 321a through 321e located below the seat 301 in the housing 327. In the illustrated embodiment the IR emitter 313 is located in an alcove 331 above the safety interlock device 303 and the IR detectors (321a-321e) are located in an alcove 335 below the safety interlock device 303. The IR detectors 321a through 321e are spaced apart a distance such that the infrared radiation that is diffracted by the opening 307 impinges on the IR detectors. It is understood that the IR emitter 313 could be below the safety interlock device 303 and that the IR detectors 321a-321e could be above the safety interlock device or in some other arrangement without departing from the scope of this invention. A visible light emitter and array of visible light detectors (not shown) could be used in place of the IR emitter 313 and IR detectors 321a-321e.

In the embodiment of FIG. 12, the infrared radiation from the IR emitter 313 diffracted by the safety interlock device 303 so that the infrared radiation from the IR emitter is detected by the IR detectors 321a thru 321e when the interlock device 303 is properly located on the seat 301. The number of detectors 321a-321e may be other than shown in this embodiment without departing from the scope of the present invention. When the interlock device 303 is not present, infrared radiation from the IR emitter 313 is seen by the middle IR detector 321c (broadly, a second detector), but not by the other detectors 321a, 321b, 321d, 321e. The interlock device 303 is preferably keyed (not shown) to the housing 327 to assure proper positioning. A visible light detector (not shown) may also be used to detect ambient visible light as in earlier embodiments of the invention.

Figure 13:
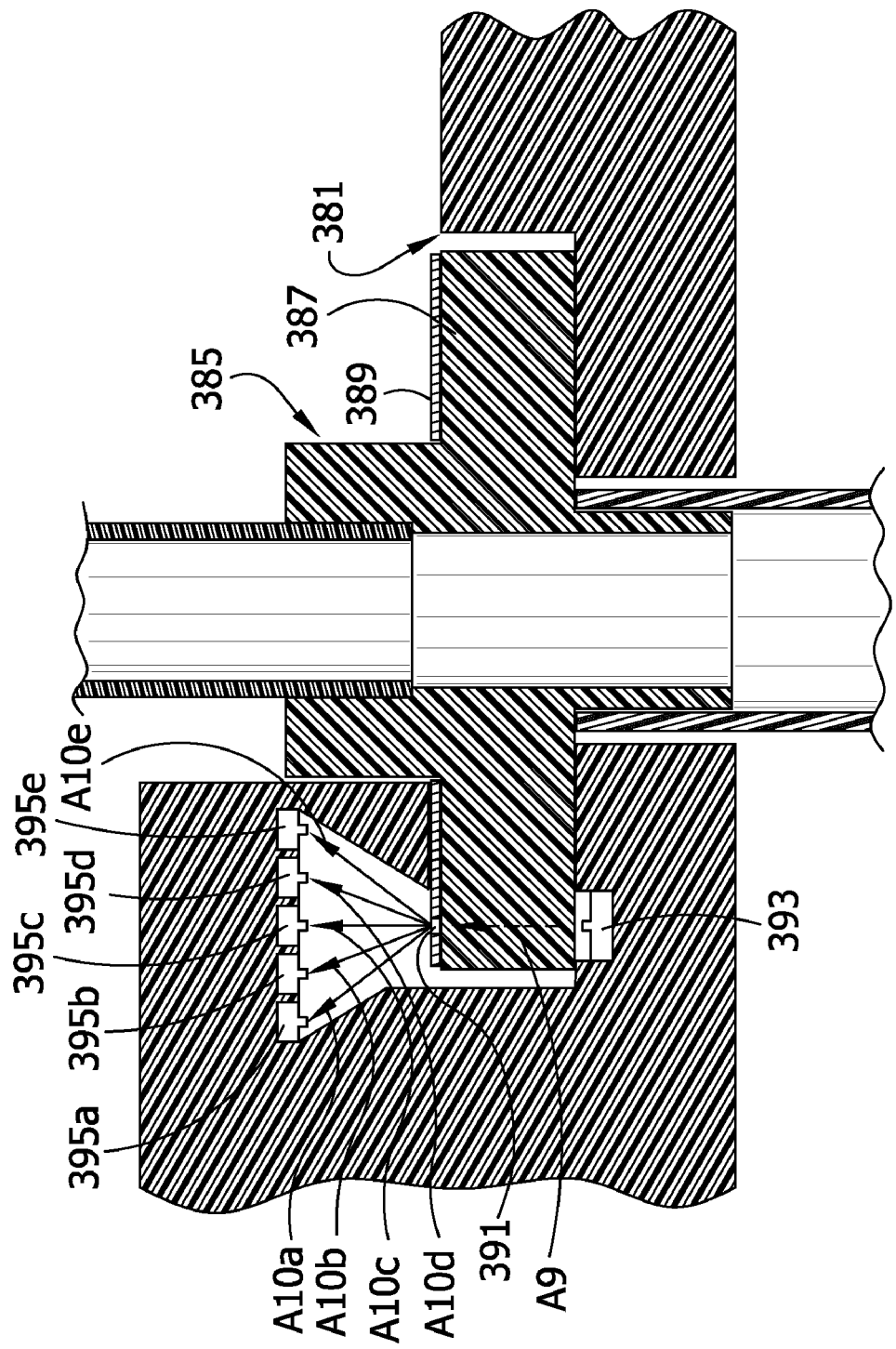
FIG. 13 is an enlarged, fragmentary section of a pump and a safety interlock device of an eighth embodiment.

FIG. 13 shows a seat 381 and a safety interlock device 385 of an eighth embodiment of the present invention. In this embodiment, the safety interlock device 385 has an electromagnetic radiation propagation affecting member 387 made of a material capable of transmitting infrared radiation. The electromagnetic radiation propagation affecting member 387 has a layer of material 389 on the top surface of the member that is opaque to the transmission of IR. The opaque layer 389 has an opening 391 that breaks the single infrared radiation beam A9 from the IR emitter 393 via diffraction into a series of spaced apart beams A10a through A10e that are detected by respective IR detectors 395a through 395e when the safety interlock device 385 is properly seated in the pump. When the propagation affecting member 387 is removed from the seat 381, only the IR detector 395c sees the infrared radiation from the IR emitter 393. It will be understood that the number of IR detectors 395a-395e may be other than shown. It is further understood an IR detector other than IR detector 395c can see infrared radiation or more than one IR detector can see the infrared radiation when the propagation affecting member 387 is removed from the seat 381. One can also switch the orientation of the group of IR detectors 395a-395e to be in the lower portion of seat 381 and the IR emitter or IR emitters in the upper portion of the seat. A visible light emitter and visible light detectors (not shown) could be used in place of the IR emitter 393 and IR detectors 395a-395e. In that event, the electromagnetic radiation propagation member would be capable of transmitting visible light, but have a layer (like layer 389) that is opaque to visible light. Moreover, another visible light detector could be used in this eighth embodiment as in prior embodiments. The interlock device 385 is preferably keyed (not shown) to assure proper positioning.

Figure 14:
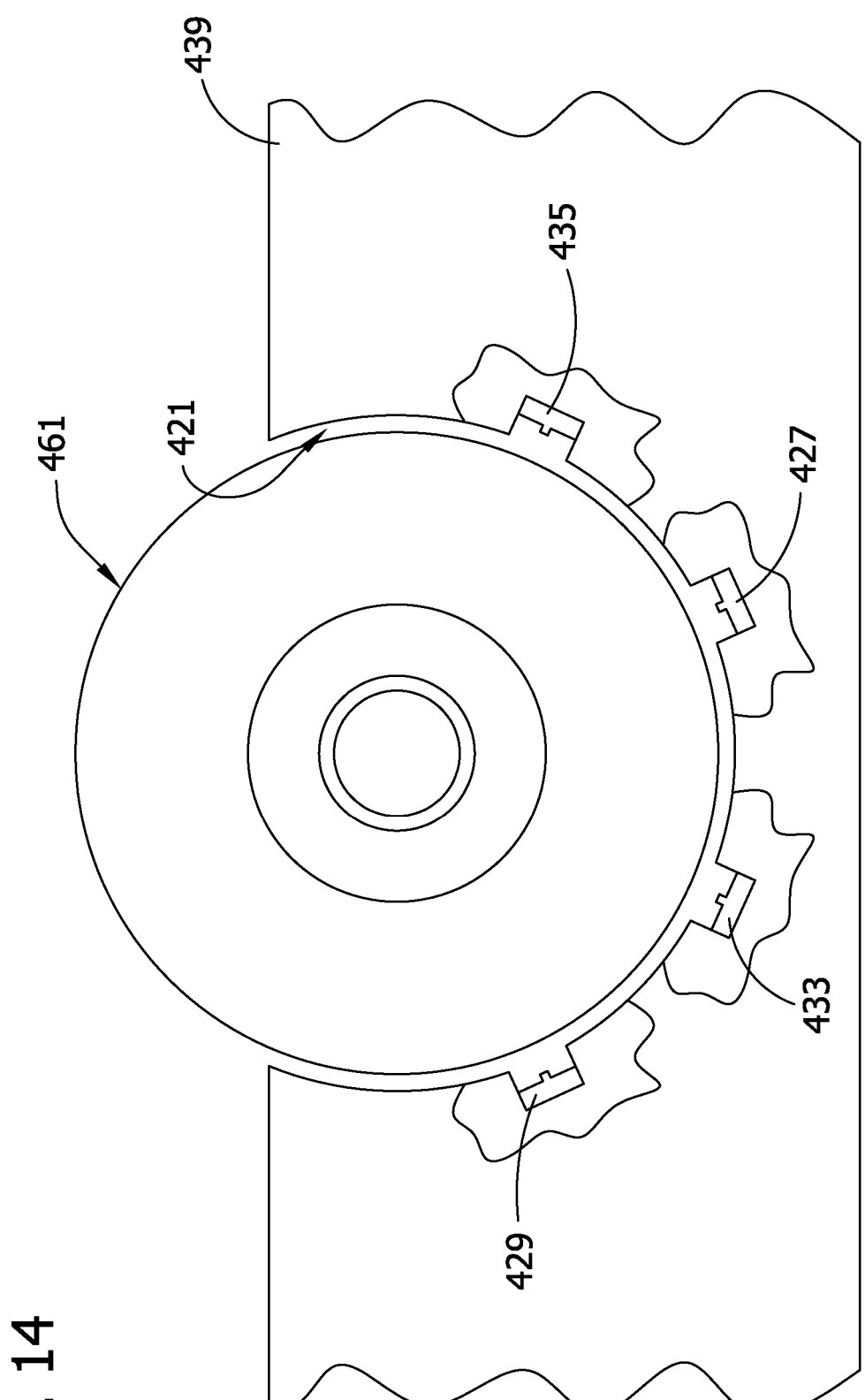
FIG. 14 is a top plan view of a pump and a safety interlock device of a ninth embodiment.

FIG. 14 shows a seat 421 and a safety interlock device 461 of a ninth embodiment of the present invention. The seat 421 is part of a pump 401 that is illustrated in block diagram form in FIG. 16. The pump 401 mounts a feeding set 405 including tubing 455 and a safety interlock device 461. The feeding set 405 may be substantially the same as the feeding set 5 shown in FIG. 3. A pumping device 423 includes a rotor 437 driven by a motor 425. The rotor 437 can engage the tubing 455 to pump fluid to a patient, substantially as described in previous embodiments. This embodiment includes an IR emitter 427, an IR detector 429, a visible light emitter 433, and a visible light detector 435 in respective alcoves in the housing 439 (FIG. 14). In this embodiment, the IR emitter 427 and the IR detector 429 are arranged at an approximately 90 degree angle with respect to each other and the visible light emitter 433 and the visible light detector 435 are arranged at an approximately 90 degree angle with respect to each other. Other relative angles are also possible. Generally speaking, the IR detector 429 is located relative to the IR emitter 427 so that in the absence of the safety interlock device 461, the infrared radiation emitted by the IR emitter will not impinge upon the IR detector. Both the IR emitter 427 and visible light emitter 433 are arranged generally perpendicular to the immediately adjacent side of the safety interlock device 461 when properly mounted on the pump 401. Moreover in this and other embodiments, the gap between the emitters 427, 433 and the safety interlock device 461 is preferably small in relation to the diameter of the safety interlock device (e.g., nominally 0.005 inches or about 0.13 mm). The safety interlock device 461 of this embodiment is transmissive to infrared radiation but is opaque to visible light. In other words, the interlock device 461 filters out visible light but passes infrared radiation.

The infrared signal emitted by the IR emitter 427 is diffused and reflected in the safety interlock device 461 such that the signal strikes the IR detector 429 when the feeding set 405 is properly loaded. The seat 421 and safety interlock device 461 of this embodiment are especially useful in operating in a dark room since the visible light emitter 433 provides a second electromagnetic radiation signal (e.g., a blue light) that substitutes for visible light not present in a dark room. The control system of this embodiment first pulses the IR emitter 427 until the IR detector 429 receives a signal recognizing that the safety interlock device 461 is loaded. Next, the visible light emitter 433 is activated to send a light signal that is blocked by the safety interlock device 461 if the safety interlock device is correctly located in the seat 421. The visible light detector 435 is operated to check for the visible light signal and to detect excess ambient light. If either condition is detected (i.e., light from emitter 433 or excess ambient light), a controller 477 activates an alarm that warns the operator to check the alignment of the feeding set 405 and does not allow the pump 401 to operate until the condition is corrected. The blockage of ambient light by the safety interlock device 461 causes the controller 477 to recognize that the set is loaded and the pump may be operated. The pump 401 detects a fault condition if the visible light detector 435 detects the visible light signal from the visible light emitter 433 after the IR detector 429 detects the presence of the safety interlock device 461.

Figure 16:
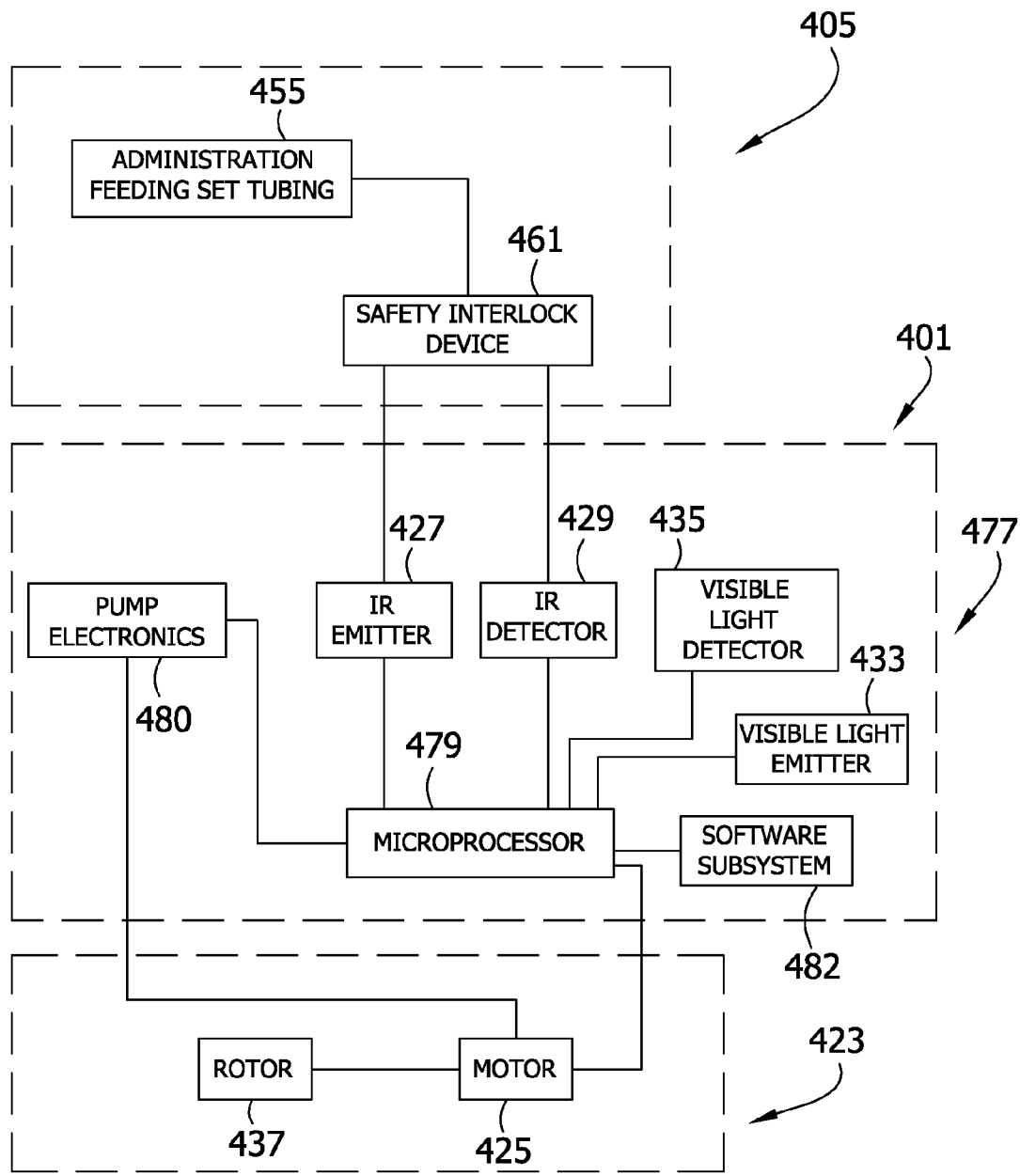
FIG. 16 is a block diagram showing a feeding set and elements of the pump of the ninth embodiment.

Referring to FIG. 16, the controller 477 has a microprocessor 479 that controls pump electronics 480 that operate the motor 425. The controller 477 includes at least one software subsystem 482 used in detecting the proper positioning of the feeding set 405 on the pump 401. Operation of the software subsystem 482 for use in controlling the pump 401 based on whether the feeding set 405, and in particular the safety interlock device 461, is properly positioned on the pump, is given in a flowchart illustrated in FIG. 17. This particular set of instructions operates so that the IR emitter 427 is turned on and off or "pulsed". When the pump 401 is powered up at 1396, the software initializes at block 1398 by setting several items to OFF. For example, the IR emitter 427 and visible light emitter 433 are set to OFF. Similarly, a program feature called Ambient Lock is set to OFF, as are program features InstantOutput and Output. Briefly, Ambient Lock is a feature that is triggered to prevent operation of the pump 401 when it is determined that the IR detector 429 sees infrared radiation from a source other than the IR emitter 427. The InstantOutput is a temporary or preliminary output of the software (i.e., whether the pump 401 is to be allowed to begin pumping). Output is the final output of the software used for determine whether the pump 401 is permitted to operate for pumping fluid.

Figure 17:
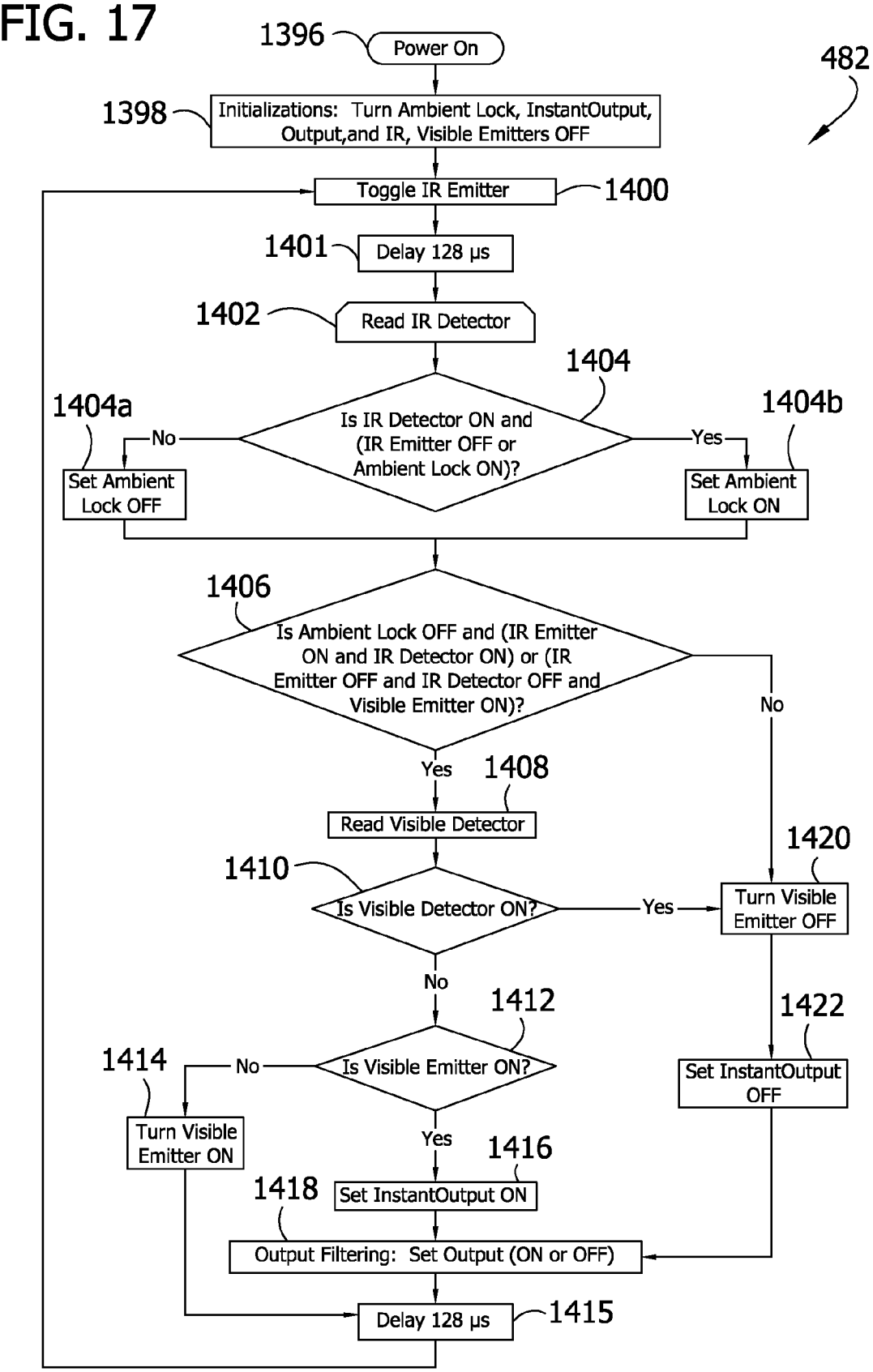
FIG. 17 is a flow chart showing operation of a software subsystem used with the pump of the ninth embodiment that pulses an infrared emitter.

At the outset as shown in FIG. 17, the function of the software subsystem 482 will be described assuming that the safety interlock device 461 has been properly positioned on the pump 401. After the initialization 1398, the IR emitter 427 is switched (or "toggled") ON at block 1400 so that infrared radiation is emitted. If the safety interlock device 461 is positioned so that the infrared radiation strikes the safety interlock device, the propagation of the infrared radiation from the emitter 427 will be affected so that infrared radiation is diffused and reflected within the safety interlock device. Some of the infrared radiation exits the safety interlock device and strikes the IR detector 429. The software pauses briefly at block 1401 after the IR emitter 427 is toggled on and then reads the IR detector 429 at block 1402 to determine if it is "ON" (i.e., that infrared radiation is detected). The software subsystem 482 then proceeds to a decision block 1404 where it queries whether the IR detector 429 is ON and either the IR emitter 427 is OFF or the Ambient Lock is ON. In the case where the safety interlock device 461 is properly positioned, the IR detector 429 is ON, but the IR emitter 427 is ON and the Ambient Lock is OFF. Therefore, the answer to the query at decision block 1404 is "no". In other words, the IR detector 429 has seen infrared radiation from the emitter 427, which is indicative of proper positioning of the safety interlock device. The software then sets the Ambient Lock to OFF at block 1404a (which is no change from its initialized condition) and proceeds to another decision block 1406.

In the next decision block 1406, the software subsystem 482 can operate to bypass evaluation of the visible light detector 435 in a situation where either the Ambient Lock is ON (because infrared radiation was detected by detector 429 when the IR emitter 427 was OFF), or where the IR emitter 427, IR detector 429 and visible light emitter 433 are all OFF. In the present case, Ambient Lock is OFF and both the IR emitter 427 and IR detector 429 are ON, so the software proceeds to read the visible light detector 435 at block 1408. The properly located safety interlock device 461 blocks the visible light detector 435 so the reading is OFF. Thus when queried at the next decision block 1410, the answer is "no" and the program moves to the next decision block 1412. The visible light emitter 433 has not been turned on yet so the program causes the visible light emitter to be turned on at block 1414 and moves to the end of the program where there is a delay 1415. The InstantOutput and Output were both initialized to OFF so that the pump 401 is not allowed to run. After the delay at 1415, the program returns to step 1400. The intermittent operation of the IR emitter 427 and conditional operation of the visible light emitter 433 provides significant power savings in operation of the pump 401. This feature is helpful when the pump 401 is operated on battery power.

Proceeding back to the toggling step 1400, the IR emitter 427 is now turned OFF and the IR detector 435 reads OFF when it is queried at 1404 after the delay. As a result, the Ambient Lock stays OFF so that when the next decision block 1406 is reached the answer is again in the affirmative and the visible light detector 435 is read once again at 1408. The safety interlock device 461 still blocks the visible light detector 435 so the visible light detector is OFF. Unlike the first loop through the program steps, the visible light emitter 433 is now on so the program moves on to set the InstantOutput to ON at block 1416, indicating that the pump 401 should be allowed to operate for pumping fluid. However, the program may not immediately allow the pump 401 to operate. As indicated in the next action block 1418, output filtering may be used before the final Output is given. For instance, the software may require at block 1418 that there be a number of occurrences of the InstantOutput 1416 being set to ON before the final Output 1418 is set to ON. Various algorithms for establishing confidence in the final output of the program could be employed. On the other hand, output filtering could be omitted in which case the Output 1418 would be equivalent to the InstantOutput 1416 in every instance. In either case, once the Output 1418 is set to ON, the pump 401 is allowed to operate. Once operation of the pump 401 is permitted, a routine for checking to make sure the safety interlock device 461 remains in position can be executed. In the illustrated embodiment, this is accomplished by continued operation of software subsystem 482. It is also envisioned that the visible light emitter 433 could be turned off again to conserve power. Various ways of operating the IR emitter 427 and visible light emitter 433 intermittently can be employed within the scope of the present invention.

It will be appreciated that there are several circumstances in which the software subsystem 482 would prevent operation of the pump 401 by detecting fault conditions indicative of the safety interlock device 461 of the feeding set 405 not being properly positioned on the pump. Reference is also made to FIG. 15 showing several conditions that can occur from the implementation of the software instructions found in the software subsystem 482. The conditions shown are not intended to be exhaustive, but representative of likely conditions to occur in the operation of the pump 401. Until such time as the IR detector 429 detects infrared radiation (IR detector "ON"), the software subsystem 482 will not allow the pump 401 to operate. In other words, Output 1418 will never be set to ON until after the IR detector 429 has at least once detected infrared radiation. If the IR detector 429 has never been ON, when the software reaches decision block 1406, the answer will be "no" and the program will proceed to the end of the loop with Instant Output 1422 set to OFF. Similarly, the visible emitter 433 will not be turned on at 1414 until a point after infrared radiation from the IR emitter 427 has been detected by the IR detector 429. In that case, the software subsystem 482 proceeds from decision block 1406 to turn the visible emitter 433 is OFF (block 1420) and the InstantOutput is set to OFF (block 1422).

In the first condition or state of FIG. 15, both the IR emitter 427 and IR detector 429 are OFF. This may occur, for example if the IR emitter 427 had been ON, but the IR detector 429 did not detect infrared radiation in a previous loop of the software subsystem 482 shown in FIG. 17. This would occur, for example if the feeding set 405 has not been installed. At decision block 1406, the answer to the query would have been "no", so the program would have set InstantOutput 1422 to OFF and passed to the end of the loop. In a second loop, the IR emitter 427 is toggled OFF so that now both the IR emitter and IR detector 429 are OFF as shown in condition 1. This is an indication that the feeding set 405 is not in place on the pump 401 (a "fault" condition). We note that the condition XX in the table of FIG. 15 is meant to indicate not applicable or inactive for the particular component in the specific condition described.

The second condition of FIG. 15 is the first of the conditions in which the feeding set 405 and safety interlock 461 would be detected. Previously, the software subsystem 482 would have cycled through a loop in which the visible light emitter 433 would have been turned on at 1414. This prior program loop is represented by condition 6 in which the IR emitter 427 and IR detector 429 are ON, but the visible light emitter 433 has not yet been energized so that Output is not yet allowed at block 1418 to be set to ON. In the second loop, the IR emitter 427 and IR detector 429 are OFF, but when the program reaches block 1408 the visible light detector 435 is read. Assuming the feeding set 405 is properly in position, the visible light detector 435 will not be ON so that the software subsystem 482 finds the feeding set properly positioned and sets Output 1418 to ON so that the pump 401 may operate. Condition 8 recognizes that in a later loop of the software subsystem 482 the IR emitter 427, IR detector 429 and visible light emitter 433 may all be ON, but that a reading of OFF for the visible light detector 435 still allows results in Output 1418 being set to ON. Conditions 3 and 9 are similarly parallel, but in these conditions the visible light detector 435 detects light emitted from the visible light emitter 433, thus preventing the pump 401 from being activated to pump fluid to a patient.

Condition 4 illustrates a situation in which ambient electromagnetic radiation in the environment surrounding the pump 401 is detected by the IR detector 429. The IR emitter 427 is OFF, so the software subsystem 482 may know that the infrared radiation is not coming from the IR emitter. In that event, the software subsystem 482 receives a "yes" answer to the query at block 1404 and then sets AMBIENT LOCK to ON in block 1404b. As a result, the software subsystem 482 bypasses at block 1406 any evaluation of the presence of visible light and sets InstantOutput to OFF at 1422. In condition 5, the safety interlock device 461 is not in place so that the initial reading at block 1402 of the IR detector 429 with the IR emitter 427 ON will be that the IR detector is OFF. The software subsystem 482 will immediately proceed after block 1406 through blocks 1420 and 1422 to set Output (at block 1418) to OFF without any further evaluation of visible light. The pump 401 may also be configured to indicate there is a BRIGHT ambient light condition such as might occur if the pump was placed in or near a window in home use. The indication of bright ambient light would instruct the user to move the pump to a lower light location.

The software subsystem 482 is also capable of detecting a condition in which there is excessively bright ambient light. As shown in condition 7, the IR emitter 427 and IR detector 429 are both ON, which is indicative of the feeding set 405 being properly positioned on the pump 401. In fact, the set 405 either has not been properly loaded, or an improper set that does not block visible light has been loaded. However, although the visible light emitter 433 is OFF, the visible light detector 435 detects visible light. The software subsystem 482 proceeds at decision block 1410, when the visible light detector 435 is ON, to block 1420 and 1422 so InstantOutput is set to OFF and the pump 401 cannot run.

Figure 18:
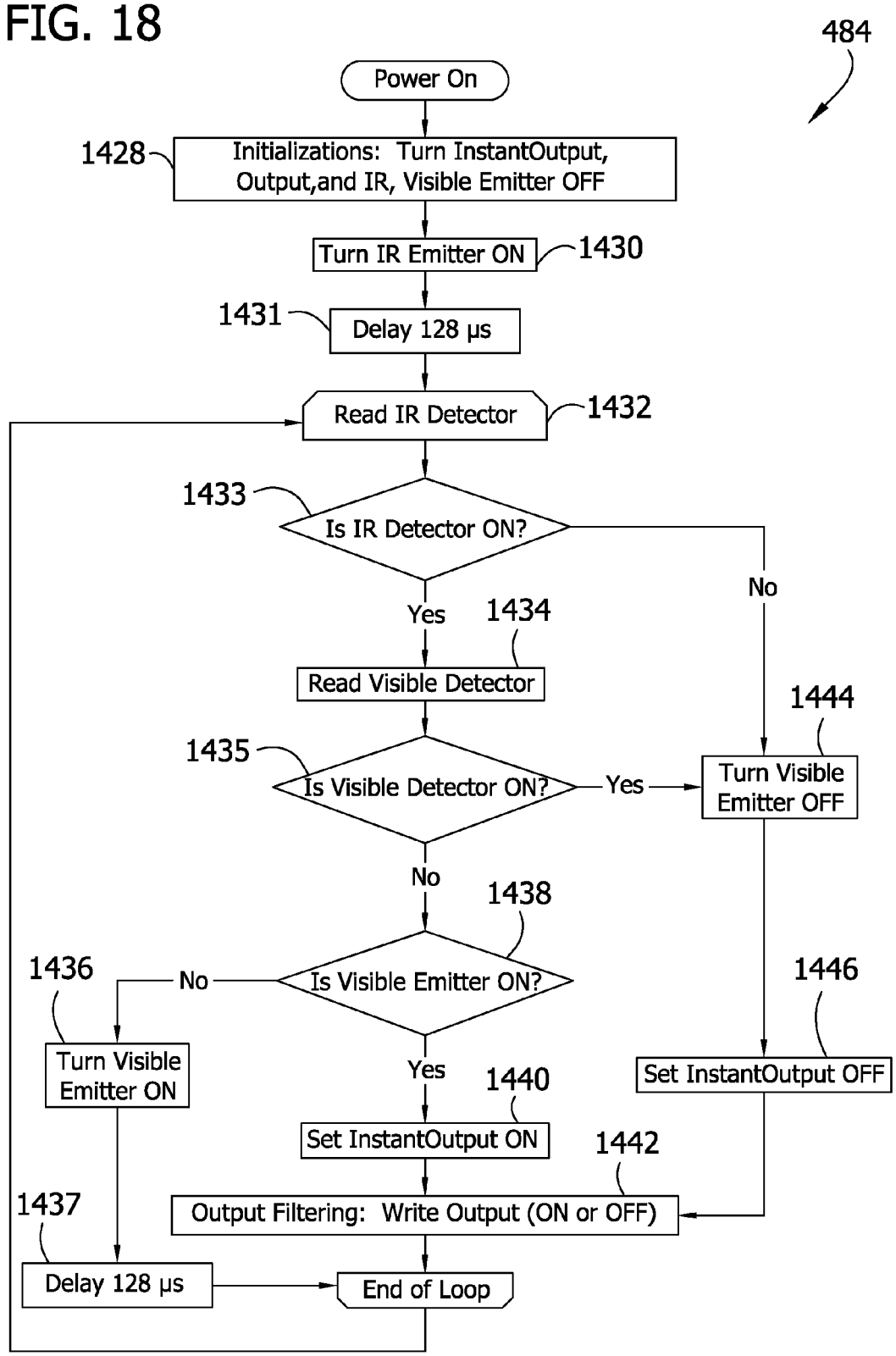
FIG. 18 is a flow chart showing operation of another software subsystem that can be used with the pump of the ninth embodiment that does not pulse the infrared emitter.

Another software subsystem 484 that could be used to operate the controller 477 of the pump 401 is illustrated in FIG. 18. In this system for detecting proper placement of the feeding set 405 including the safety interlock device 461, the IR emitter 427 is not turned off and on (i.e., it is not "pulsed").

Thus after the initialization step 1428, the IR emitter 427 is turned on at block 1430 and remains on while the pump 401 is powered. As illustrated in condition 1 in the table of FIG. 19 showing selected operating conditions of the software subsystem 484 of FIG. 18, the only time the IR emitter 427 is OFF is when the pump 401 is not yet turned on. Referring again to FIG. 18, the software subsystem 484 delays at block 1431 after the IR emitter 427 is turned on before reading the IR detector 429 at block 1432. The software subsystem 484 conditions any further checks for confirming the feeding set is properly positioned on the detection of infrared radiation by the IR detector 429 at block 1433. Condition 2 illustrates the situation where the IR emitter 427 is on, but infrared radiation is not detected by the IR detector 429. Once the IR detector 429 detects infrared radiation, the program proceeds in a first loop to read the visible light detector 435 at block 1434 to make certain the visible light detector is OFF (block 1435), and then turns the visible light emitter 433 ON at block 1436. After a delay at block 1437, the software subsystem 484 proceeds to a second loop in which the software subsystem 484 confirms that visible light is blocked at 1435 and because the visible light emitter 433 is found to be ON at 1438 sets InstantOutput to ON at block 1440. Assuming no further output filtering, Output is set to ON at block 1442 and the pump 401 is permitted to operate. However if visible light is detected (i.e., at block 1434) prior to activation of the visible light emitter 433, the visible light emitter is prevented from being turned on. In that case, the software subsystem 484 will proceed to block 1444 to turn the visible light emitter 433 off, and at block 1446 to set InstantOutput to OFF. Detection of visible light by the visible light detector 435 prior to activation of the visible light emitter is shown in condition 3 of FIG. 19.

Figure 20:
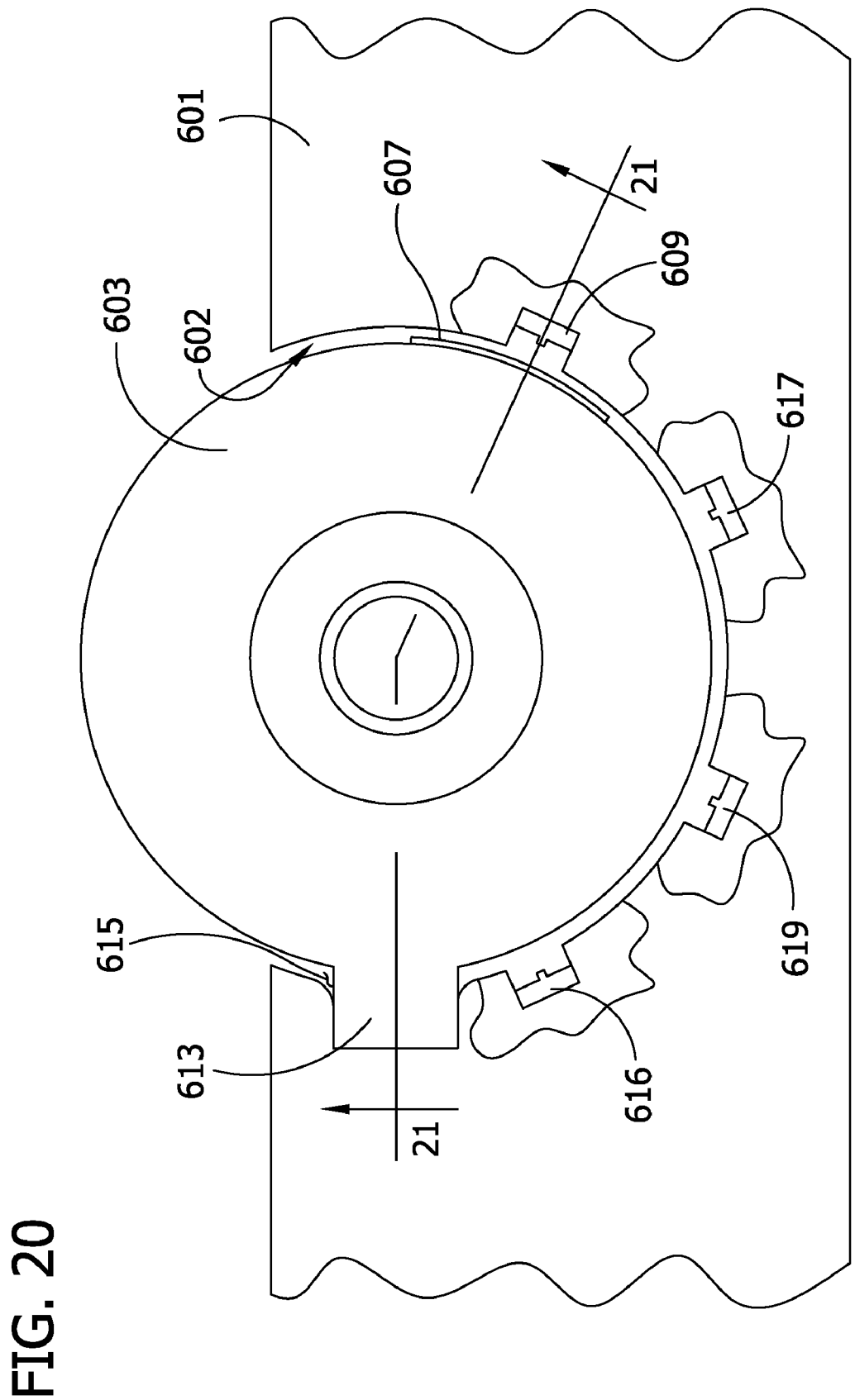
FIG. 20 is a fragmentary top plan view of a pump and safety interlock device of a tenth embodiment.
Figure 21:
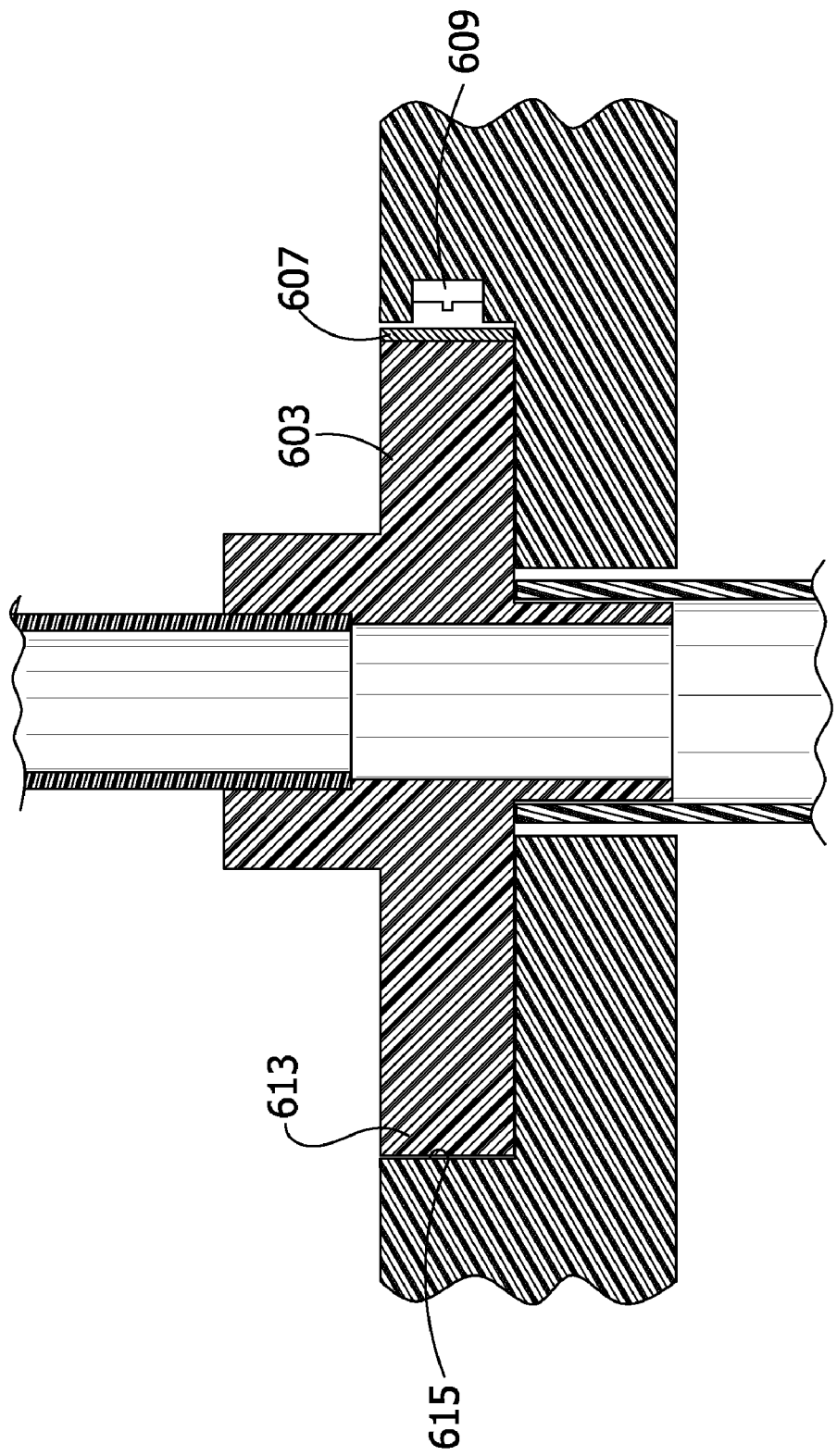
FIG. 21 is an enlarged fragmentary section taken along line 21-21 of FIG. 20.

Conditions 4 and 6 both result in the software subsystem 484 setting Output 1442 to ON and allowing the pump 401 to operate because the feeding set and safety interlock device 461 are detected. Conditions 5 and 7 illustrate circumstances in which the detection of visible light by the visible light detector 435 prevents operation of the pump even though infrared radiation has been detected by the IR detector 429. In condition 7, the visible light detector 435 may be detecting either light from the visible light emitter 433 or from ambient. In either case, the pump 401 is not permitted to operate. In FIGS. 17 and 18 other variations may be described by tracing a path through the flow chart, as shown FIGS. 20 and 21 show a fragmentary portion of a pump 601 adjacent a seat 602 of the pump, and safety interlock device 603 of a tenth embodiment of the present invention. The safety interlock device 603 comprises a material that transmits both infrared radiation and visible light. The safety interlock device 603 includes a blocking portion 607 that is opaque to the transmission of visible light so that the visible light is not transmitted to the visible light detector 609 when the safety interlock device is loaded on the pump. The safety interlock device 603 includes a key 613 that is received in a corresponding slot 615 in the pump housing so that the safety interlock device 603 must be aligned with the blocking portion 607 generally adjacent the visible light detector. In the illustrated embodiment, the key 613 is a protrusion extending from the safety interlock device 603 but it is understood that the key and the corresponding slot 615 could be other shapes and sizes without departing from this invention. Other structures for keying the position of a safety interlock device in a pump may be used within the scope of the present invention.

When the safety interlock device 603 is loaded in the pump 601 infrared electromagnetic radiation from the IR emitter 616 is diffused and reflected through the safety interlock device and detected by the IR detector 617 to verify that the set has been loaded. Next, the visible light detector 609 will check for visible light in the pump 601 will not detect any because of the location of the blocking portion 607 of the safety interlock device 603 that blocks visible light. In the embodiment of FIG. 20, the visible light emitter 619 will be emitted, sending a visible light signal into the safety interlock device 603. The visible light signal will not be transmitted to the visible light detector 609 because of the present of the blocking portion 607 and the control system of the pump 601 will allow the pump to operate.

Figure 22:
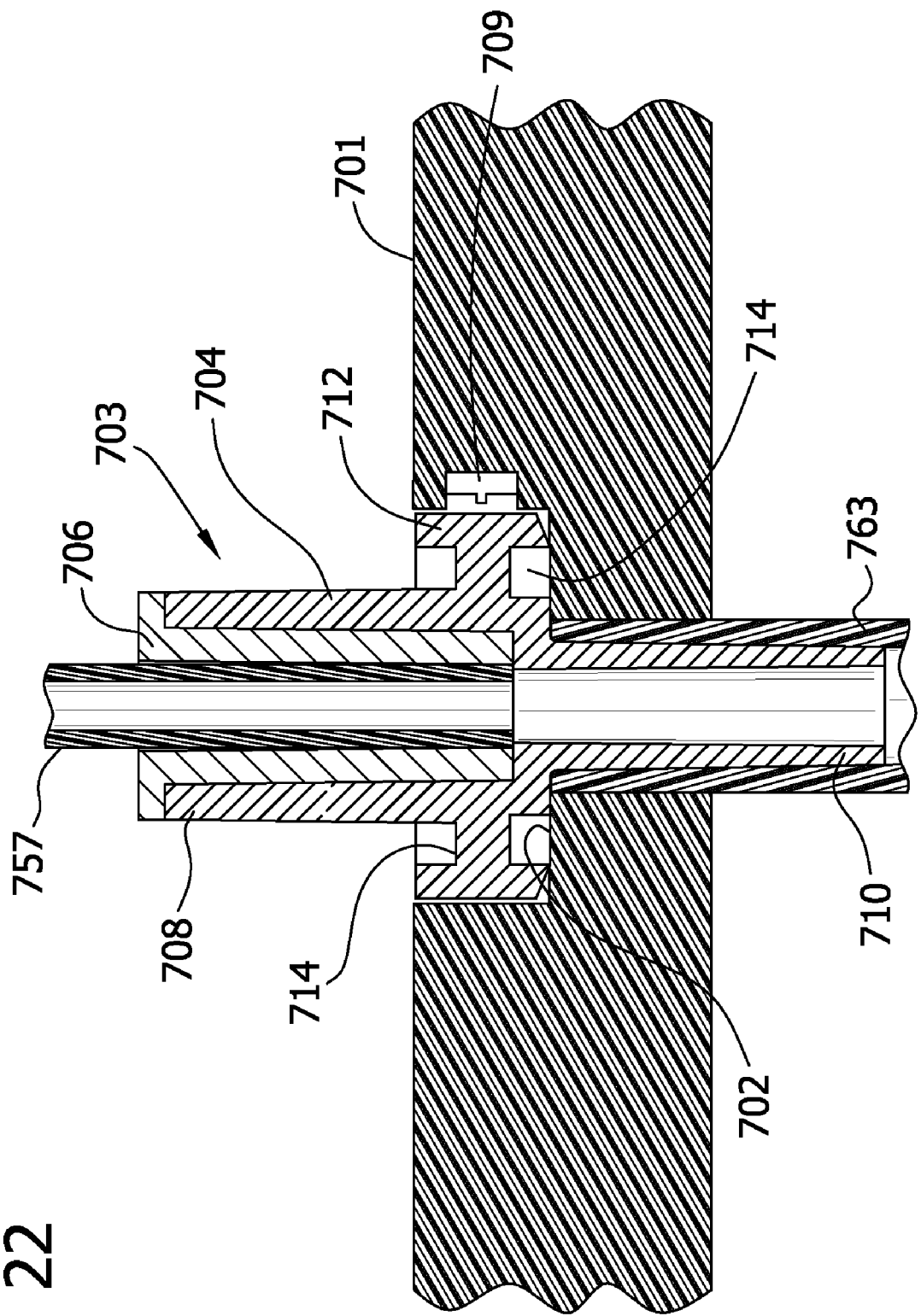
FIG. 22 is an enlarged, fragmentary section similar to FIG. 21 but showing a safety interlock device of an eleventh embodiment.

FIG. 22 shows a fragmentary section of a pump 701 including a seat 702, and safety interlock device 703 of an eleventh embodiment of the present invention. The safety interlock device 703 is made of a material that transmits infrared radiation, but blocks electromagnetic radiation in the visible range so that the visible light is not transmitted to a visible light detector 709 when the safety interlock device is loaded on the pump 701. Other suitable constructions for passing electromagnetic radiation of one wavelength and blocking electromagnetic radiation of another wavelength may be employed within the scope of the present invention. An arrangement of visible and infrared emitters and detectors like that shown in FIG. 20 may be employed in the eleventh embodiment, although different arrangements are also possible.

The safety interlock device 703 comprises an outer member 704 and an inner member 706. The outer member includes an upper tubular portion 708, a lower tubular portion 710 and an annular flange 712. The annular flange has upper and lower annular channels 714. In the illustrated embodiment, the channels allow less material to be used, but have no effect on the operation of the safety interlock device 703. A first tube section 757 of a feeding set is received in the upper portion 708 of the outer member 704 of the safety interlock device 703 and a second tube section 763 is received over the lower portion 710 of the outer member.

The outer member 704 is made of the material that selectively blocks visible light and passes infrared radiation. The inner member 706 can be made of the same material as the outer member, or of a different material. However, the inner member 706 is substantially opaque to electromagnetic radiation in the infrared range and also in the visible range, and is also preferably highly reflective. In the illustrated embodiment, the inner member 706 is made of the same material as the outer member 704, but is white in color. The inner member 706 can be formed as one piece with the outer member 704, such as by a dual injection or extrusion process. Additionally, the outer and inner members 704, 706 could be made as separate pieces and attached to each other in a suitable manner such as bonding or welding. The inner member 706 is positioned in the optical path of the infrared radiation that enters the safety interlock device 703, and is disposed between the infrared radiation path and first tube section 757. Accordingly, an outer surface of the inner member 706 defines an "inner boundary region" in this eleventh embodiment for reflecting infrared radiation. The inner member 706 inhibits the loss of internal reflection of infrared radiation that might be caused by the presence of certain liquids (e.g., water) flowing in the tube 757. Thus, a strong reflection of infrared radiation to the infrared radiation detector (not shown) can be made regardless of the optical characteristics of the fluid flowing through the tube 757.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A pumping apparatus and pump set for use to deliver a supply of liquid to a patient, the pump set comprising a conduit for the liquid and a safety interlock device associated with the conduit, the pumping apparatus comprising:
   a pumping device operable to act on the pump set to drive flow of the liquid in the pump set;
   a control system for controlling operation of the pumping device;
   at least two electromagnetic radiation detecting sensors operatively connected to the control system of the pumping apparatus, a first of said sensors being positioned on the pumping apparatus for identifying the safety interlock device in a loaded position of the device and configured to send a signal to the control system indicating the safety interlock device is properly loaded on the pumping apparatus, and a second of said sensors being positioned on the pumping apparatus for detecting a fault condition associated with the positioning of the safety interlock device and configured to send a signal to the control system indicating the safety interlock device is not properly loaded on the pumping apparatus, the first sensor being configured to indicate that the safety interlock is properly loaded on the pumping apparatus only when electromagnetic radiation is detected by the first sensor and the second sensor being configured to indicate that the safety interlock is not properly loaded on the pumping device only when electromagnetic radiation is detected by the second sensor;
   wherein said safety interlock device transmits infrared radiation through the safety interlock device and blocks visible light.

2. The pumping apparatus and pump set as set forth in claim 1 wherein the safety interlock device diffuses infrared radiation to guide it to the first sensor.

3. The pumping apparatus and pump set as set forth in claim 1 wherein said first sensor is an infrared detector and said second sensor is a visible light detector.

4. The pumping apparatus and pump set as set forth in claim 3 further comprising an infrared source operatively connected to the control system of the pumping apparatus and adapted to transmit infrared radiation through the safety interlock device in the loaded position of the device, the infrared sensor being located out of alignment with the infrared detector.

5. The pumping apparatus and pump set as set forth in claim 3 further comprising a visible light source operatively connected to the control system of the pumping apparatus for sending a visible light signal used to detect said fault condition of the pumping apparatus.

6. The pumping apparatus and pump set as set forth in claim 3 wherein the infrared source is operated intermittently to generate a pattern of emitter activations in which infrared radiation is emitted from the infrared source.

7. The pumping apparatus and pump set as set forth in claim 1 wherein the pumping apparatus has a key formation permitting the safety interlock device to be mounted on the pump only in a predetermined orientation.

* * * * *